United States Patent
Loccufier et al.

(10) Patent No.: US 8,362,101 B2
(45) Date of Patent: Jan. 29, 2013

(54) MULTIFUNCTIONAL TYPE II PHOTOINITIATORS AND CURABLE COMPOSITIONS

(75) Inventors: Johan Loccufier, Zwijnaarde (BE); Jaymes Van Luppen, Wilrijk (BE)

(73) Assignee: Agfa Graphics NV, Mortsel (BE)

( * ) Notice: Subject to any disclaimer, the term of this patent is extended or adjusted under 35 U.S.C. 154(b) by 277 days.

(21) Appl. No.: 12/992,610

(22) PCT Filed: May 28, 2009

(86) PCT No.: PCT/EP2009/056517
§ 371 (c)(1),
(2), (4) Date: Nov. 15, 2010

(87) PCT Pub. No.: WO2009/147054
PCT Pub. Date: Dec. 10, 2009

(65) Prior Publication Data
US 2011/0069130 A1    Mar. 24, 2011

Related U.S. Application Data

(60) Provisional application No. 61/059,815, filed on Jun. 9, 2008.

(30) Foreign Application Priority Data

Jun. 5, 2008 (EP) .................................. 08104267

(51) Int. Cl.
| | |
|---|---|
| B41J 2/01 | (2006.01) |
| C07C 229/34 | (2006.01) |
| C07C 229/66 | (2006.01) |
| C07C 225/16 | (2006.01) |
| C07D 409/12 | (2006.01) |
| C07D 403/12 | (2006.01) |
| C07D 335/16 | (2006.01) |
| B05D 3/06 | (2006.01) |
| C08F 2/46 | (2006.01) |

(52) U.S. Cl. .............. 522/46; 522/65; 549/27; 564/328; 560/52; 427/487

(58) Field of Classification Search .............. 549/27; 564/328; 560/52; 522/46, 53, 65; 427/487
See application file for complete search history.

(56) References Cited

FOREIGN PATENT DOCUMENTS

| CN | 1594369 A | 3/2005 |
|---|---|---|
| EP | 1 674 499 A1 | 6/2006 |
| JP | 2004-224993 A | 8/2004 |
| WO | 03/033492 A1 | 4/2003 |

OTHER PUBLICATIONS

STN structure search (Sep. 24, 2012).*
Official Communication issued in International Patent Application No. PCT/EP2009/056517, mailed on Aug. 31, 2009.
Jiang et al., "Copolymeric Dendritic Macrophotoinitiators," Polymer, Sep. 22, 2005, vol. 46, No. 24, pp. 11079-11084.
Loccufier et al., "Polymerizable Type II Photoinitiators and Curable Compositions,", U.S. Appl. No. 12/922,611, filed Nov. 15, 2010.

* cited by examiner

Primary Examiner — Vu A Nguyen
(74) Attorney, Agent, or Firm — Keating & Bennett, LLP

(57) ABSTRACT

A multifunctional Type II photoinitiator according to Formula (I):

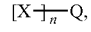

Formula (I)

wherein X represents a structural moiety according to Formula (II):

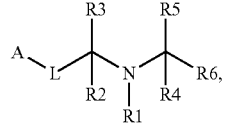

Formula (II)

wherein:
A represents a Norrish Type II initiating group; and L represents a divalent linking group positioning the Norrish Type II initiating group A and the CR2R3-group in a 1-5 to a 1-9 position wherein position 1 is defined as the first atom in the aromatic or alicyclic ring of A to which L is covalently bonded and the position 5 to 9 is defined as the carbon atom of the CR2R3-group to which L is covalently bonded, with the proviso that L does not contain an amine. Radiation curable compositions and inks include the multifunctional Type II photoinitiator.

14 Claims, No Drawings

MULTIFUNCTIONAL TYPE II PHOTOINITIATORS AND CURABLE COMPOSITIONS

BACKGROUND OF THE INVENTION

1. Field of the Invention

The present invention relates to a new class of multifunctional Type II photoinitiators, especially suitable for food compliant radiation curable formulations, more specifically in radiation curable inks and inkjet inks.

2. Description of the Related Art

A free radical photoinitiator is a chemical compound that initiates a polymerization of monomers when exposed to actinic radiation by the formation of a free radical. Photoinitiators are frequently used in UV-curable compositions, such as UV curable inkjet inks.

Two types of free radical photoinitiators can be distinguished. A Norrish Type I initiator is an initiator which cleaves after excitation, yielding the initiating radical immediately. A Norrish type II-initiator is a photoinitiator which is activated by actinic radiation and forms free radicals by hydrogen abstraction from a second compound that becomes the actual initiating free radical. This second compound is called a polymerization synergist or co-initiator.

A photoinitiator can be a monofunctional compound, but can also be a multifunctional compound, i.e. having more than one photoinitiating group. WO 03/033492 (COATES BROTHERS) discloses multifunctional thioxanthone photoinitiators.

When radiation curable compositions are used for food packaging, toys and dental applications, the amount of extractable residues is a critical issue and needs to be minimized. Low molecular weight products are usually not completely built into the polymer network and are prone to be readily extracted or to diffuse out of the cured composition.

Especially Norrish type II initiators are a point of concern regarding extractable residues. Norrish type II photo-initiators always require a co-initiator. Aliphatic tertiary amines, aromatic amines and thiols are preferred examples of co-initiators. After transfer of a hydrogen atom to the Norrish type II initiator, the radical generated on the synergist initiates the polymerization. Theoretically the co-initiator is built into the polymer network. However, it is highly unlikely that both the hydrogen transfer and the initiation reaction yields are a hundred percent. Side reactions are likely to occur leaving unreacted synergist and side products in the composition. In food packaging printed upon with such a radiation curable composition, these low molecular weight residues remain mobile and if toxic will cause health risks upon being extracted into the food.

One approach to minimize extraction of the photoinitiator is to use a photoinitiator having one or more ethylenically unsaturated polymerizable groups so that it can be copolymerized with the other monomers of the radiation curable composition. However the copolymerization reduces the mobility of the photoinitiator and a reduction in curing speed can be observed.

JP 2004-224993 (NIPPON KAYAKU) discloses self-photopolymerization type photopolymerization initiators used in radiation curable compositions for reducing its evaporation from a cured film.

Another approach in solving the extraction problem is to design Norrish Type II initiators with a higher molecular weight. However, polymeric initiators have a certain tendency to lose reactivity. Hence, often considerable amounts of polymeric initiators are required in order to reach the desired curing speed thereby also increasing the viscosity to an undesirable level for a great number of applications with radiation curable compositions, e.g. inkjet inks and lacquers.

EP 1674499 A (AGFA GRAPHICS) discloses radiation curable compositions and photoreactive polymers including a dendritic polymer core with at least one initiating functional group and at least one co-initiating functional group. While the use of a dendritic polymer core is advantageous for maintaining a low viscosity of the radiation curable composition, an improvement in curing speed is still desirable, especially in the absence of nitrogen inertisation.

CN 1594369 A (UNIV SHANGHAI JIAOTONG) discloses a branch-shape macromolecular type thioxanthone photoinitiator and preparation method thereof, which consists of, using 2-mercaptobenzoic acid, substituted phenol, epichlorohydrin as raw material to synthesize thioxanthene ketone having double epoxy radicals, then dissolving thioxanthene ketone and polypropyleneimine dendroid high polymer into dissolvent, elevating the temperature for several hours to polymerize, thus obtaining macromolecule thioxanthone photo-initiator.

JIANG XUESONG, et al. Copolymeric dendritic macrophotoinitiators. Polymer Elsevier Science Publishers B.V., 21 Nov. 2005, vol. 46, no. 24, p. 11079-11084, discloses copolymeric dendritic macrophotoinitiators containing thioxanthone and octene moieties on a poly(propylene imine) dendrimer.

Therefore, there still remains a need for photoinitiators, combining a high reactivity, without the need for nitrogen inertisation and a low impact on the viscosity of the formulation, while still maintaining a low amount of extractable residues.

SUMMARY OF THE INVENTION

According to preferred embodiments of the present invention, a new class of multifunctional Type II photoinitiators is disclosed, especially suitable for food compliant radiation curable formulations.

According to a further preferred embodiment of the present invention, radiation curable compositions and inks including these multifunctional Type II photoinitiators are disclosed.

These and other preferred embodiments of the present invention will become apparent in the description hereinafter.

It was surprisingly found that that a multifunctional Type II photoinitiator according to Formula I, in the absence of a co-initiator or a blanket of nitrogen as oxygen depletion unit, gave a superior curing speed and a low viscosity in radiation curable formulations while maintaining low levels of migratable residues.

Preferred embodiments of the invention have been realised with a multifunctional photoinitiator as defined below.

Further advantages and preferred embodiments of the present invention will become apparent from the following description.

DETAILED DESCRIPTION OF THE PREFERRED EMBODIMENTS

Definitions

The term "dye", as used in disclosing the present invention, means a colorant having a solubility of 10 mg/L or more in the medium in which it is applied and under the ambient conditions pertaining.

The term "pigment" is defined in DIN 55943, herein incorporated by reference, as a colorant that is practically insoluble in the application medium under the pertaining ambient conditions, hence having a solubility of less than 10 mg/L therein.

The term "C.I." is used in disclosing the present application as an abbreviation for Colour Index.

The term "alkyl" means all variants possible for each number of carbon atoms in the alkyl group i.e. for three carbon atoms: n-propyl and isopropyl; for four carbon atoms: n-butyl, isobutyl and tertiary-butyl; for five carbon atoms: n-pentyl, 1,1-dimethyl-propyl, 2,2-dimethylpropyl and 2-methylbutyl etc.

The terms "weight %", "wt %" and "weight percentage" all have the same meaning.

Multifunctional Type II Photoinitiators

A multifunctional Type II photoinitiator according to a preferred embodiment of the present invention includes from 2 to 8 photoinitiating groups, preferably from 2 to 6 photoinitiating groups and most preferably from 2 to 4 photoinitiating groups. For example, the multifunctional Type II photoinitiator can have two benzophenone groups. Also different photoinitiating groups can be used in the multifunctional Type II photoinitiator, e.g. one or more benzophenone groups and one or more thioxanthone groups. Using different photoinitiating groups results in an enlarged absorption spectrum for curing. This is especially useful when colorants are used in the radiation curable compositions that absorb partly in the same spectral region.

The multifunctional Type II photoinitiator according to a preferred embodiment of the present invention can be represented by Formula (I):

Formula (I)

wherein X represents a structural moiety according to Formula

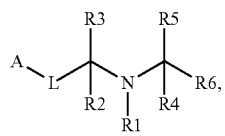

Formula (II)

wherein:
A represents a Norrish Type II initiating group;
L represents a divalent linking group positioning the Norrish Type II initiating group A and the CR2R3-group in a 1-5 to a 1-9 position wherein position 1 is defined as the first atom in the aromatic or alicyclic ring of A to which L is covalently bonded and the position 5 to 9 is defined as the carbon atom of the CR2R3-group to which L is covalently bonded, with the proviso that L does not contain an amine;
R1 represents an optionally substituted group selected from the group consisting of an alkyl group, an alkenyl group, an alkynyl group, an aralkyl group, an alkaryl group, an aryl group and a heteroaryl group;
R2 to R6 each independently represent a hydrogen or an optionally substituted group selected from the group consisting of an alkyl group, an alkenyl group, an alkynyl group, an aralkyl group, an alkaryl group, an aryl group and a heteroaryl group, with the proviso that at least one of R2 to R6 represents a hydrogen;
any two or three groups of the group selected from R1 to R6 and L may represent the necessary atoms to form a five to eight membered ring; and with the proviso that none of L, R1 to R6 is substituted with a (meth)acrylate group;

Q represents a n-valent linking group having a number average molecular weight of at most 5,000;

Q is bonded to each of the moieties X via a single bond to a group selected from R1 to R6, L and A; and n represents an integer from 2 to 8.

In a preferred embodiment, none of R1 to R6 is substituted with an ethylenically unsaturated polymerizable group. In a more preferred embodiment the multifunctional Norrish Type II photoinitiator is a non-polymerizable multifunctional Norrish Type II photoinitiator.

In a preferred embodiment, the Norrish Type II initiating group A is selected from the group consisting of a substituted or unsubstituted benzophenone and a substituted or unsubstituted thioxanthone.

In a preferred embodiment Q represents an n-valent linking group with the integer n representing 2, 3 or 4.

In a preferred embodiment Q is bonded to each of the moieties X via a single bond to a group selected from R1 to R6, more preferably to the group R6.

In a more preferred embodiment, the multifunctional Type II photoinitiator includes an optionally substituted benzophenone and an optionally substituted thioxanthone. This advantage thereof is a broader absorption spectrum of the photoinitiator resulting in a higher curing speed for a radiation curable ink and a more uniform curing speed for different coloured inks in an ink set.

Preferred Norrish Type II initiating groups A are given below in Table 1, without being limited thereto. The dotted line represents the chemical bond to the divalent linking group L.

TABLE 1

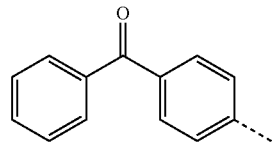

A1

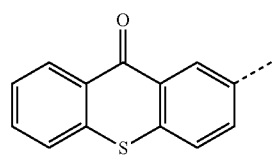

A2

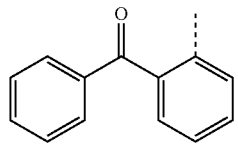

A3

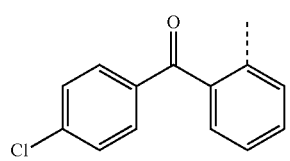

A4

TABLE 1-continued

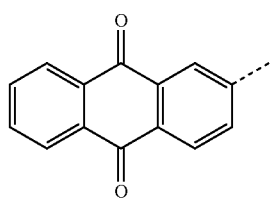 A5

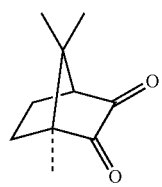 A6

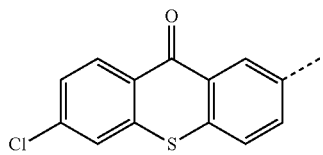 A7

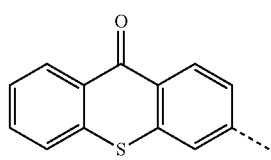 A8

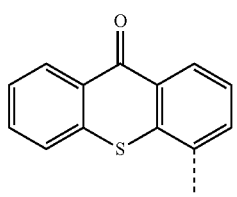 A9

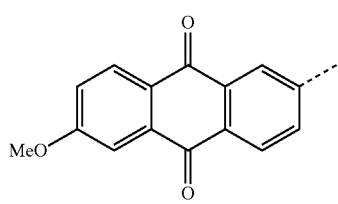 A10

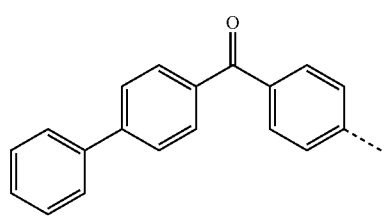 A11

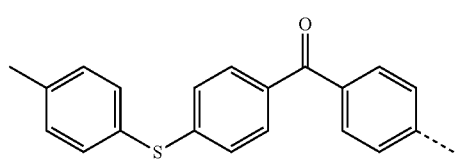 A12

TABLE 1-continued

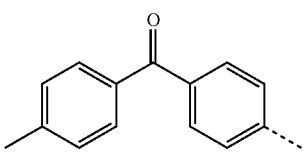 A13

In a particularly preferred embodiment, the n-valent linking group Q includes at least one ethylene oxide and/or propylene oxide moiety.

The n-valent linking group Q has a number average molecular weight of at most 5,000, making it suitable for low viscosity applications, such as inkjet or lacquers.

In a further particularly preferred embodiment, R1 is selected from the group consisting of a substituted or unsubstituted alkyl group and a substituted or unsubstituted aryl group.

In another particularly preferred embodiment R1 represents an aryl group according to Formula (III):

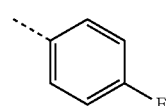 Formula (III)

where the dotted line represents the chemical bond to the nitrogen atom in Formula (II) and wherein E represents a group selected from the group consisting of an ester, an aldehyde, a ketone and an amide. An ester group is particularly preferred.

It was found to be essential for improving curing speed that the Norrish Type II initiating group A and the CR2R3-group are in a 1-5 to a 1-9 position wherein position 1 is defined as the first atom in the aromatic or alicyclic ring of A to which L is covalently bonded and the position 5 to 9 is defined as the carbon atom of the CR2R3-group to which L is covalently bonded, with the proviso that L does not contain an amine. The curing speed decreased with a factor 3 to 4 when the CR2R3-group was placed in a 1-3 or a 1-4 position. The curing speed drops drastically when the CR2R3-group is positioned further away from the Norrish Type II initiating group A, e.g. in a 1-10 position. In the most preferred embodiment, the CR2R3-group is positioned in a 1-5 position.

A nitrogen atom may be present in the divalent linking group L in a form differing from an amine, e.g. as an amide group. This is shown below in Table 2 by the photoinitiators INI-14 and INI-20.

In a preferred embodiment, the divalent linking group L is represented by the group —O—(CH$_2$)$_n$— wherein n represents an integer selected from 3 to 7.

Preferred examples of photoinitiators according to preferred embodiments of the present invention, having a 2 to 8 valent linking group Q are given in Table 2 below without being limited thereto.

TABLE 2
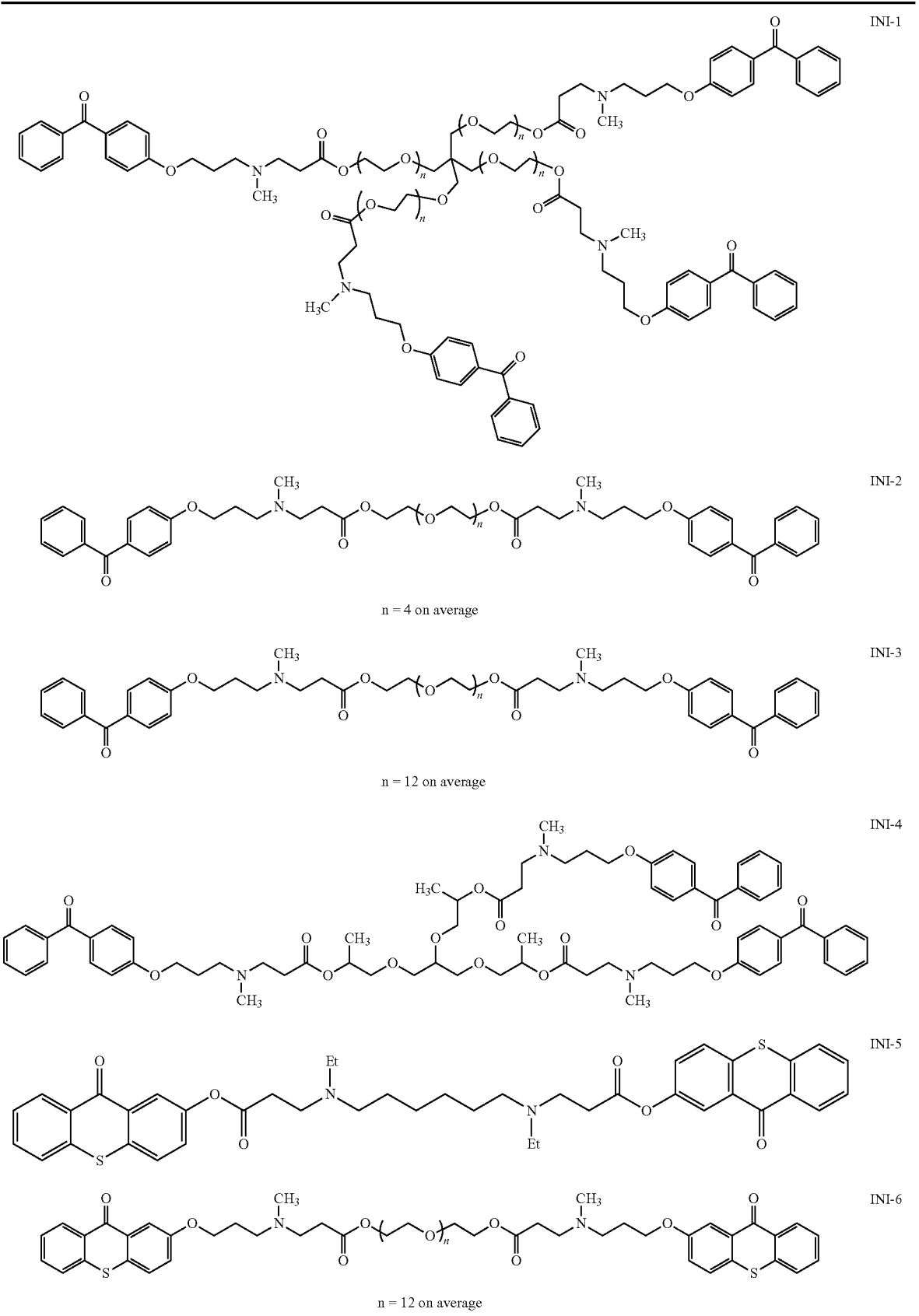

TABLE 2-continued
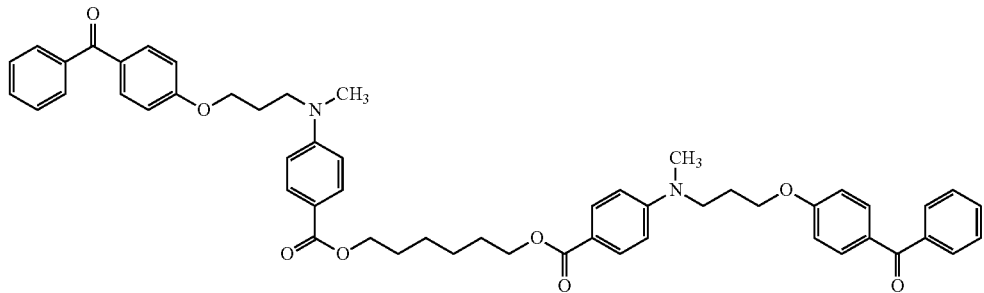 [SMILES: CN(CCCOc1ccc(C(=O)c2ccccc2)cc1)c1ccc(C(=O)OCCCCCCOC(=O)c2ccc(N(C)CCCOc3ccc(C(=O)c4ccccc4)cc3)cc2)cc1]
INI-7
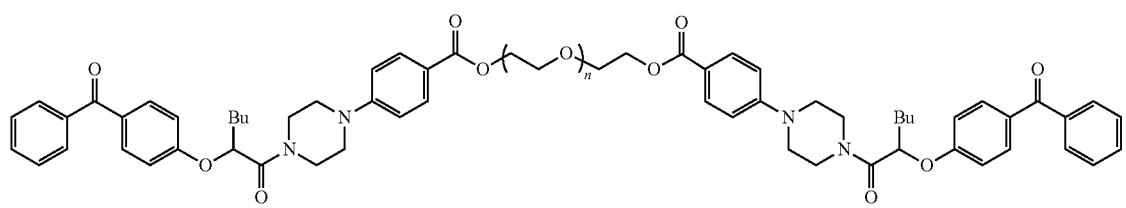
INI-8
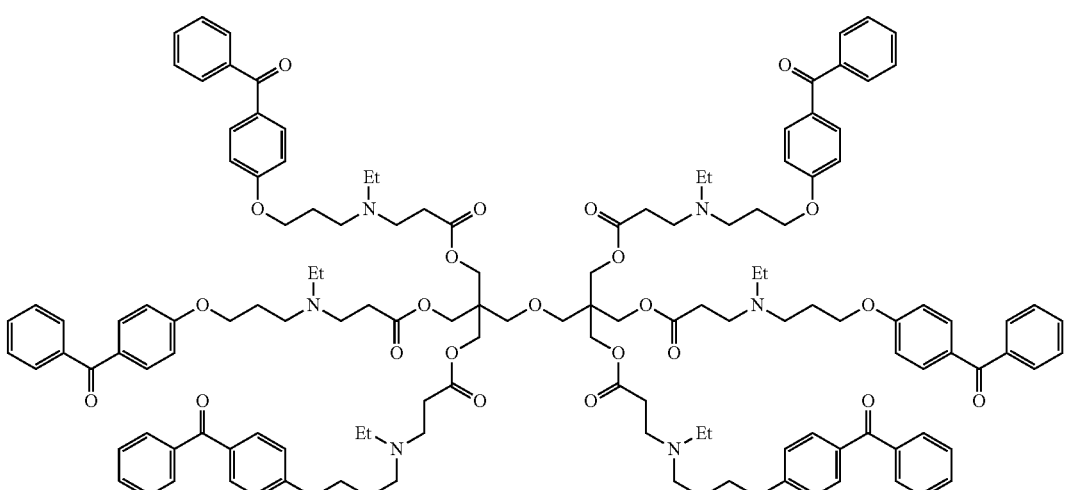
INI-9
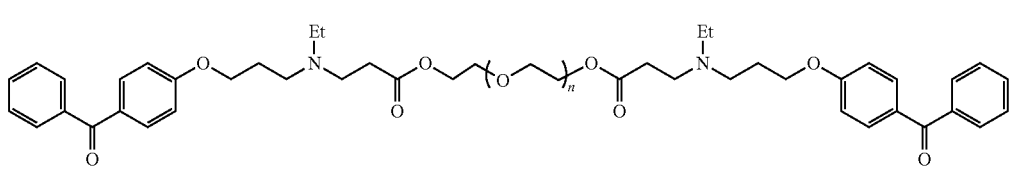
INI-10
n = 12 on average
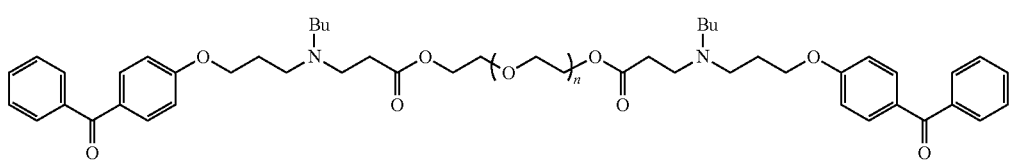
INI-11
n = 12 on average
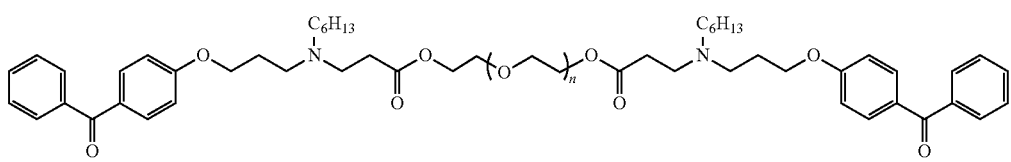
INI-12
n = 12 on average TABLE 2-continued
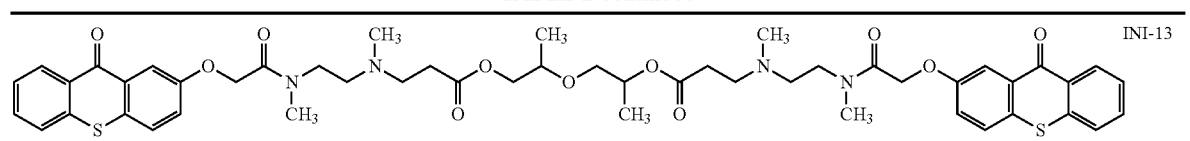
INI-13
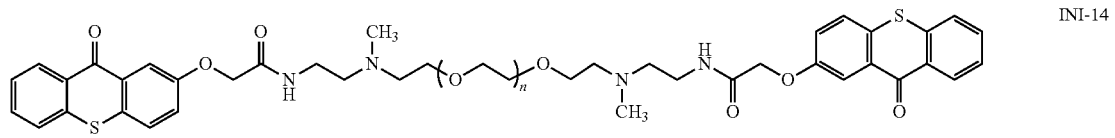
INI-14
n = 4 on average
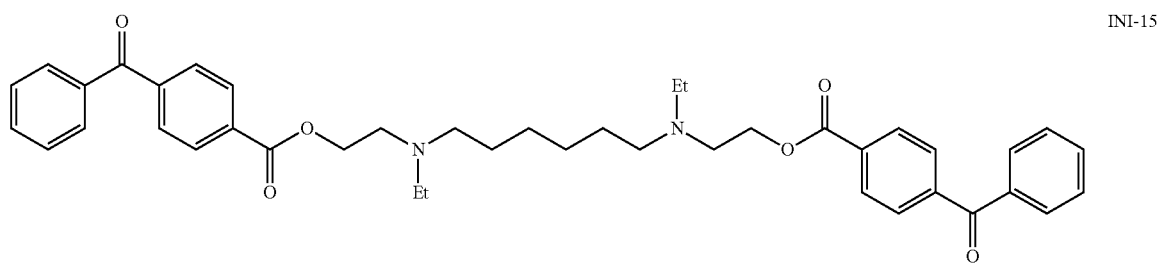
INI-15
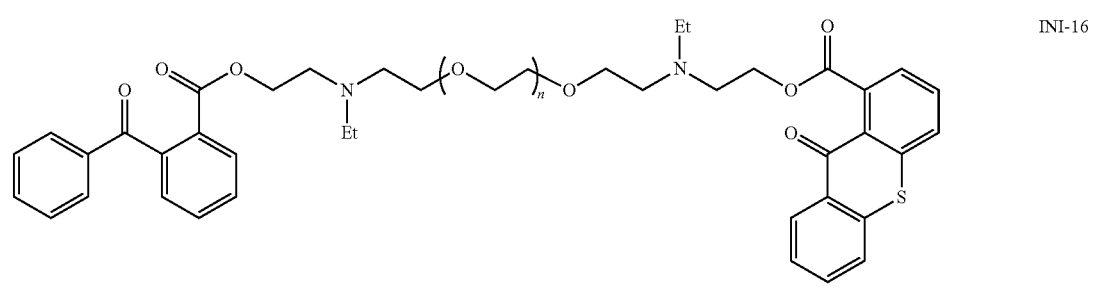
INI-16
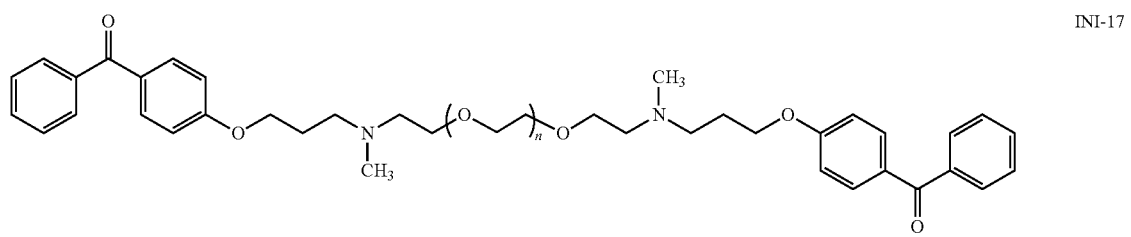
INI-17
n = 4 on average
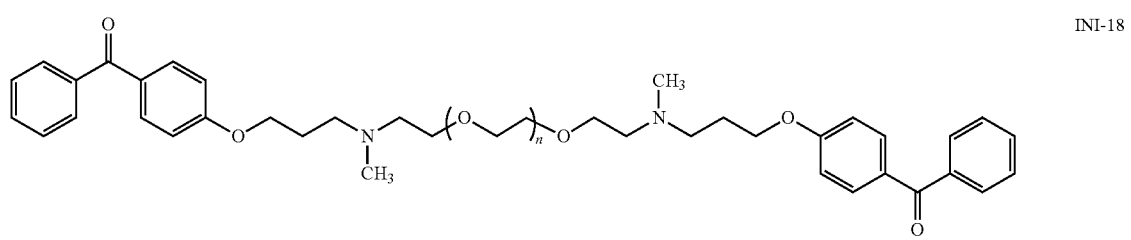
INI-18
n = 12 on average
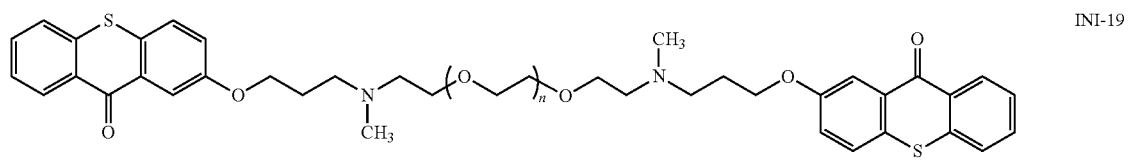
INI-19
n = 12 on average TABLE 2-continued

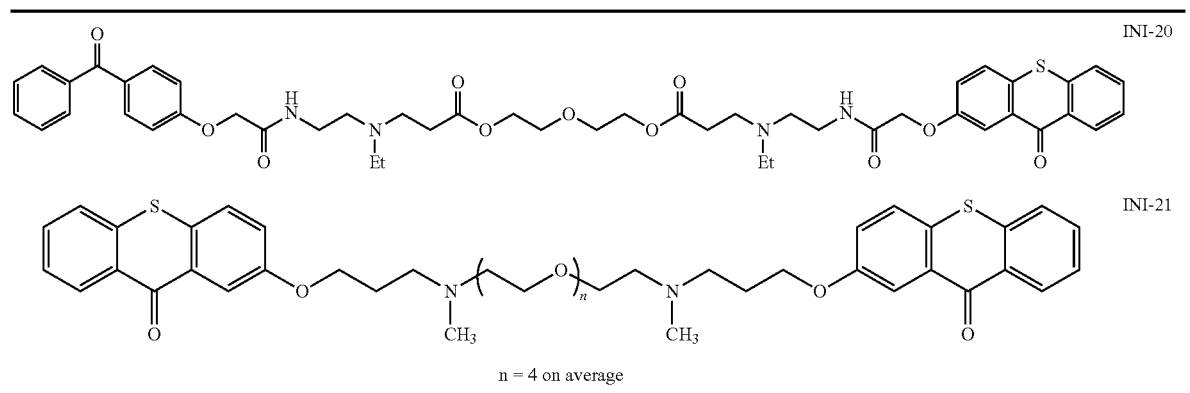

n = 4 on average

Radiation Curable Liquids and Inks

The radiation curable liquids and inks are preferably cured by UV radiation and are preferably radiation curable inkjet liquids or inks. The radiation curable liquids and inks can also be advantageously used in offset printing, screen printing, flexographic printing and other printing or coating techniques.

The radiation curable liquids and inks are preferably non-aqueous liquids or inks. The term "non-aqueous" refers to a liquid carrier which should contain no water. However sometimes a small amount, generally less than 5 wt % of water based on the total weight of the liquid or ink, can be present. This water was not intentionally added but came into the formulation via other components as a contamination, such as for example polar organic solvents. Higher amounts of water than 5 wt % tend to make the non-aqueous liquids and inks instable, preferably the water content is less than 1 wt % based on the total weight of radiation curable liquid or ink and most preferably no water at all is present.

The radiation curable liquids and inks preferably do not contain an evaporable component such as an organic solvent. But sometimes it can be advantageous to incorporate a small amount of an organic solvent to improve adhesion to the surface of a substrate after UV-curing. In this case, the added solvent can be any amount in the range that does not cause problems of solvent resistance and VOC, and preferably 0.1-10.0 wt %, and particularly preferably 0.1-5.0 wt %, each based on the total weight of the curable liquid or ink.

The radiation curable liquids and inks are preferably part of an ink set, more preferably an inkjet ink set, including at least one ink containing one or more colorants, preferably one or more colour pigments. The curable ink set preferably includes at least one yellow curable ink (Y), at least one cyan curable ink (C) and at least one magenta curable ink (M) and preferably also at least one black curable ink (K). The curable CMYK-ink set may also be extended with extra inks such as red, green, blue, and/or orange to further enlarge the colour gamut of the image. The CMYK-ink set may also be extended by the combination of full density and light density inks of both colour inks and/or black inks to improve the image quality by lowered graininess.

The pigmented radiation curable ink preferably contains a dispersant, more preferably a polymeric dispersant, for dispersing the pigment. The pigmented curable ink may contain a dispersion synergist to improve the dispersion quality and stability of the ink. Preferably, at least the magenta ink contains a dispersion synergist. A mixture of dispersion synergists may be used to further improve dispersion stability.

The viscosity of the curable liquid and ink is preferably smaller than 100 mPa·s at 30° C. and at a shear rate of 100 $s^{-1}$. The viscosity of the radiation curable inkjet inks and liquids is preferably smaller than 30 mPa·s, more preferably lower than 15 mPa·s, and most preferably between 2 and 10 mPa·s at a shear rate of 100 $s^{-1}$ and a jetting temperature between 10 and 70° C.

The surface tension of the curable liquid and ink is preferably in the range of about 20 mN/m to about 70 mN/m at 25° C., more preferably in the range of about 22 mN/m to about 40 mN/m at 25° C.

The curable liquid or ink may further also contain at least one inhibitor.

The curable liquid or ink may further also contain at least one surfactant.

Monomers and Oligomers

The polymerizable compounds used in the radiation curable liquids and inks, especially for food packaging applications, are preferably purified compounds having no or almost no impurities, more particularly no toxic or carcinogenic impurities. The impurities are usually derivative compounds obtained during synthesis of the polymerizable compound. Sometimes, however, some compounds may be added deliberately to pure polymerizable compounds in harmless amounts, for example, polymerization inhibitors or stabilizers.

Any monomer or oligomer capable of free radical polymerization may be used as polymerizable compound. A combination of monomers, oligomers and/or prepolymers may also be used. The monomers, oligomers and/or prepolymers may possess different degrees of functionality, and a mixture including combinations of mono-, di-, tri- and higher functionality monomers, oligomers and/or prepolymers may be used. The viscosity of the radiation curable liquids and inks can be adjusted by varying the ratio between the monomers and oligomers.

Particularly preferred monomers and oligomers are monofunctional and polyfunctional acrylates, such as isoamyl acrylate, stearyl acrylate, lauryl acrylate, octyl acrylate, decyl acrylate, isoamylstyl acrylate, isostearyl acrylate, 2-ethylhexyl-diglycol acrylate, 2-hydroxybutyl acrylate, 2-acryloyloxyethylhexahydrophthalic acid, butoxyethyl acrylate, ethoxydiethylene glycol acrylate, methoxydiethylene glycol acrylate, methoxypolyethylene glycol acrylate, methoxypropylene glycol acrylate, phenoxyethyl acrylate, tetrahydrofurfuryl acrylate, isobornyl acrylate, 2-hydroxyethyl acrylate, 2-hydroxypropyl acrylate, 2-hydroxy-3-phenoxypropyl acrylate, vinyl ether acrylate, vinyl ether ethoxy(meth)acrylate, 2-acryloyloxyethylsuccinic acid, 2-acryloxyethylphthalic acid, 2-acryloxyethyl-2-hydroxyethyl-phthalic acid, lactone modified flexible acrylate, and t-butylcyclohexyl acrylate, triethylene glycol diacrylate, tetraethylene glycol diacrylate, polyethylene glycol diacrylate, dipropylene glycol diacrylate, tripropylene glycol diacrylate, polypropylene glycol diacrylate, 1,4-butanediol diacrylate, 1,6-hexanediol diacrylate, 1,9-nonanediol diacrylate, neopentyl glycol diacrylate, dimethylol-tricyclodecane diacrylate, bisphenol A EO (ethylene oxide) adduct diacrylate, bisphenol A PO (propylene oxide) adduct diacrylate, hydroxypivalate neopentyl glycol diacrylate, propoxylated neopentyl glycol diacrylate, alkoxylated dimethyloltricyclodecane diacrylate and polytetramethylene glycol diacrylate, trimethylolpropane triacrylate, EO modified trimethylolpropane triacrylate, tri(propylene glycol) triacrylate, caprolactone modified trimethylolpropane triacrylate, pentaerythritol triacrylate, pentaerithritol tetraacrylate, pentaerythritolethoxy tetraacrylate, dipentaerythritol hexaacrylate, ditrimethylolpropane tetraacrylate, glycerinpropoxy triacrylate, and caprolactam modified dipentaerythritol hexaacrylate, or an N-vinylamide such as, N-vinylcaprolactam or N-vinylformamide; or acrylamide or a substituted acrylamide, such as acryloylmorpholine.

Other suitable monofunctional acrylates include caprolactone acrylate, cyclic trimethylolpropane formal acrylate, ethoxylated nonyl phenol acrylate, isodecyl acrylate, isooctyl acrylate, octyldecyl acrylate, alkoxylated phenol acrylate, tridecyl acrylate and alkoxylated cyclohexanone dimethanol acrylate.

Other suitable difunctional acrylates include alkoxylated cyclohexanone dimethanol diacrylate, alkoxylated hexanediol diacrylate, dioxane glycol diacrylate, dioxane glycol diacrylate, cyclohexanone dimethanol diacrylate, diethylene glycol diacrylate and neopentyl glycol diacrylate.

Other suitable trifunctional acrylates include propoxylated glycerine triacrylate and propoxylated trimethylolpropane triacrylate.

Other higher functional acrylates include di-trimethylolpropane tetraacrylate, dipentaerythritol pentaacrylate, ethoxylated pentaerythritol tetraacrylate, methoxylated glycol acrylates and acrylate esters.

Furthermore, methacrylates corresponding to the above-mentioned acrylates may be used with these acrylates. Of the methacrylates, methoxypolyethylene glycol methacrylate, methoxytriethylene glycol methacrylate, hydroxyethyl methacrylate, phenoxyethyl methacrylate, cyclohexyl methacrylate, tetraethylene glycol dimethacrylate, and polyethylene glycol dimethacrylate are preferred due to their relatively high curing speed and higher adhesion to an ink-receiver surface.

Furthermore, the inkjet inks may also contain polymerizable oligomers. Examples of these polymerizable oligomers include epoxy acrylates, aliphatic urethane acrylates, aromatic urethane acrylates, polyester acrylates, and straight-chained acrylic oligomers.

Suitable examples of styrene compounds are styrene, p-methylstyrene, p-methoxystyrene, β-methylstyrene, p-methyl-β-methylstyrene, α-methylstyrene and p-methoxy-β-methylstyrene.

Suitable examples of vinylnaphthalene compounds are 1-vinylnaphthalene, α-methyl-1-vinylnaphthalene, β-methyl-1-vinylnaphthalene, 4-methyl-1-vinylnaphthalene and 4-methoxy-1-vinylnaphthalene.

Suitable examples of N-vinyl compounds are N-vinylcarbazole, N-vinylpyrrolidone, N-vinylindole, N-vinylpyrrole, N-vinylphenothiazine, N-vinylacetoanilide, N-vinylethylacetoamide, N-vinylsuccinimide, N-vinylphthalimide, N-vinylcaprolactam and N-vinylimidazole.

Examples of vinyl ethers having at least one vinyl ether group include ethyl vinyl ether, n-butyl vinyl ether, isobutyl vinyl ether, octadecyl vinyl ether, cyclohexyl vinyl ether, butanediol divinyl ether, hydroxyl butyl vinyl ether, cyclohexane dimethanol monovinyl ether, phenyl vinyl ether, p-methylphenyl vinyl ether, p-methoxyphenyl vinyl ether, α-methylphenyl vinyl ether, β-methylisobutyl vinyl ether and β-chloroisobutyl vinyl ether, diethyleneglycol divinyl ether, triethylene glycol divinyl ether, n-propyl vinyl ether, isopropyl vinyl ether, dodecyl vinyl ether, diethylene glycol monovinyl ether, cyclohexanedimethanol divinyl ether, 4-(vinyloxy)butyl benzoate, bis[4-(vinyl oxy)butyl]adipate, bis[4-(vinyl oxy)butyl]succinate, 4-(vinyloxy methyl)cyclohexylmethyl benzoate, bis[4-(vinyloxy)butyl]isophthalate, bis[4-(vinyloxymethyl)cyclohexylmethyl]glutarate, tris[4-(vinyloxy)butyl]trimellitate, 4-(vinyloxy)butyl steatite, bis[4-(vinyloxy)butyl]hexanediylbiscarbamate, bis[4-(vinyloxy)methyl]cyclohexyl]methyl]terephthalate, bis[4-(vinyloxy)methyl]cyclohexyl]methyl]isophthalate, bis[4-(vinyloxy)butyl](4-methyl-1,3-phenylene)-biscarbamate, bis[4-vinyloxy)butyl](methylenedi-4,1-phenylene) biscarbamate and 3-amino-1-propanol vinyl ether.

A preferred class of monomers and oligomers are vinyl ether acrylates such as those described in U.S. Pat. No. 6,310,115 (AGFA), incorporated herein by reference. Particularly preferred compounds are 2-(2-vinyloxyethoxy)ethyl(meth) acrylate, most preferably the compound is 2-(2-vinyloxyethoxy)ethyl acrylate.

Inhibitors

The radiation curable liquids and inks may contain a polymerization inhibitor. Suitable polymerization inhibitors include phenol type antioxidants, hindered amine light stabilizers, phosphor type antioxidants, hydroquinone monomethyl ether commonly used in (meth)acrylate monomers, and hydroquinone, t-butylcatechol, pyrogallol, 2,6-di-tert.butyl-4-methylphenol may also be used.

Suitable commercial inhibitors are, for example, SUMILIZER™ GA-80, SUMILIZER™ GM and SUMILIZER™ GS produced by Sumitomo Chemical Co. Ltd.; GENORAD™ 16, GENORAD™ 18 and GENORAD™ 20 from Rahn AG; IRGASTAB™ UV10 and IRGASTAB™ UV22, TINUVIN™ 460 and CGS20 from Ciba Specialty Chemicals; FLOORSTAB™ UV range (UV-1, UV-2, UV-5 and UV-8) from Kromachem Ltd, ADDITOL™ S range (S100, S110, S120 and S130) from Cytec Surface Specialties.

The inhibitor is preferably a polymerizable inhibitor.

Since excessive addition of these polymerization inhibitors may lower the curing speed, it is preferred that the amount capable of preventing polymerization is determined prior to blending. The amount of a polymerization inhibitor is preferably lower than 5 wt %, more preferably lower than 3 wt % of the total ink or liquid.

Surfactants

The radiation curable liquids and inks may contain a surfactant. The surfactant(s) can be anionic, cationic, non-ionic, or zwitter-ionic and are usually added in a total quantity less than 20 wt % based on the total weight of the radiation curable liquids or ink and particularly in a total less than 10 wt % based on the total weight of the radiation curable liquid or ink.

Suitable surfactants include fluorinated surfactants, fatty acid salts, ester salts of a higher alcohol, alkylbenzene sulphonate salts, sulphosuccinate ester salts and phosphate ester salts of a higher alcohol (for example, sodium dodecylbenzenesulphonate and sodium dioctylsulphosuccinate), ethylene oxide adducts of a higher alcohol, ethylene oxide adducts of an alkylphenol, ethylene oxide adducts of a polyhydric alcohol fatty acid ester, and acetylene glycol and ethylene oxide adducts thereof (for example, polyoxyethylene nonylphenyl ether, and SURFYNOL™ 104, 104H, 440, 465 and TG available from AIR PRODUCTS & CHEMICALS INC.).

For non-aqueous radiation curable liquids and ink preferred surfactants are selected from fluoro surfactants (such as fluorinated hydrocarbons) and silicone surfactants. The silicones are typically siloxanes and can be alkoxylated, polyether modified, polyether modified hydroxy functional, amine modified, epoxy modified and other modifications or combinations thereof. Preferred siloxanes are polymeric, for example polydimethylsiloxanes.

In the radiation curable liquids or ink a fluorinated or silicone compound may be used as a surfactant, however, a cross-linkable surfactant would be preferred. It is therefore preferred to use a copolymerizable monomer having surface-active effects, for example, polyacrylate copolymers, silicone modified acrylates, silicone modified methacrylates, acrylated siloxanes, polyether modified acrylic modified siloxanes, fluorinated acrylates, and fluorinated methacrylates; these acrylates can be mono-, di-, tri- or higher functional (meth)acrylates.

Surfactants are known for use in the radiation curable liquids and inks to reduce the surface tension of the liquid or ink and to reduce the contact angle on the substrate, i.e. to improve the wetting of the substrate by the ink. On the other hand, the jettable fluid must meet stringent performance criteria in order to be adequately jettable with high precision, reliability and during an extended period of time. To achieve both wetting of the substrate by the ink and high jetting performance, typically, the surface tension of the ink is reduced by the addition of one or more surfactants. In the case of curable inkjet inks, however, the surface tension of the inkjet ink is not only determined by the amount and type of surfactant, but also by the polymerizable compounds, the polymeric dispersants and other additives in the ink composition.

Depending upon the application a surfactant can be used with a high, low or intermediate dynamic surface tension. Silicone surfactants are generally known to have low dynamic surface tensions while fluorinated surfactants are known to have higher dynamic surface tensions.

Useful commercially available fluorinated surfactants are for example the ZONYL™ range of fluoro-surfactants from DUPONT and the FLUORAD™ range of fluoro-surfactants from 3M.

Silicone surfactants are often preferred, especially the reactive silicone surfactants, which are able to be polymerized together with the polymerizable compounds during the curing step.

Useful commercially available silicone surfactants are often polysiloxane surfactants, especially polyether modified polysiloxanes, preferably with one or more acrylate function in order to become polymerizable.

Examples of useful commercial silicone surfactants are those supplied by BYK CHEMIE GMBH (including BYK™-302, 307, 310, 331, 333, 341, 345, 346, 347, 348, UV3500, UV3510 and UV3530), those supplied by TEGO CHEMIE SERVICE (including TEGO RAD™ 2100, 2200N, 2250, 2300, 2500, 2600 and 2700), EBECRYL™ 350 a polysilixone diacrylate and EBECRYL™ 1360 a polysiloxane hexaacrylate from CYTEC INDUSTRIES BV and EFKA™-3000 series (including EFKA™-3232 and EFKA™-3883) from EFKA CHEMICALS B.V.

Colorants

Colorants used in the radiation curable inks may be dyes, pigments or a combination thereof. Organic and/or inorganic pigments may be used. The colorant is preferably a pigment or a polymeric dye, most preferably a pigment.

The pigments may be black, white, cyan, magenta, yellow, red, orange, violet, blue, green, brown, mixtures thereof, and the like. This colour pigment may be chosen from those disclosed by HERBST, Willy, et al. Industrial Organic Pigments, Production, Properties, Applications. 3rd edition. Wiley—VCH, 2004. ISBN 3527305769.

Particular preferred pigments are:
- C.I. Pigment Yellow 1, 3, 10, 12, 13, 14, 17, 55, 65, 73, 74, 75, 83, 93, 97, 109, 111, 120, 128, 138, 139, 150, 151, 154, 155, 175, 180, 181, 185, 194 and 213.
- C.I. Pigment Red 17, 22, 23, 41, 48:1, 48:2, 49:1, 49:2, 52:1, 57:1, 81:1, 81:3, 88, 112, 122, 144, 146, 149, 169, 170, 175, 176, 184, 185, 188, 202, 206, 207, 210, 216, 221, 248, 251, 254, 255, 264, 266, 270 and 272.
- C.I. Pigment Violet 1, 2, 19, 23, 32, 37 and 39.
- C.I. Pigment Blue 15:1, 15:2, 15:3, 15:4, 15:6, 16, 56, 61 and (bridged) aluminium phthalocyanine pigments.
- C.I. Pigment Orange 5, 13, 16, 34, 40, 43, 59, 66, 67, 69, 71 and 73.
- C.I. Pigment Green 7 and 36.
- C.I. Pigment Brown 6 and 7.

Suitable pigments include mixed crystals of the above particular preferred pigments. Mixed crystals are also referred to as solid solutions. For example, under certain conditions different quinacridones mix with each other to form solid solutions, which are quite different from both physical mixtures of the compounds and from the compounds themselves. In a solid solution, the molecules of the components enter into the same crystal lattice, usually, but not always, that of one of the components. The x-ray diffraction pattern of the resulting crystalline solid is characteristic of that solid and can be clearly differentiated from the pattern of a physical mixture of the same components in the same proportion. In such physical mixtures, the x-ray pattern of each of the components can be distinguished, and the disappearance of many of these lines is one of the criteria of the formation of solid solutions. A commercially available example is Cinquasia Magenta RT-355-D from Ciba Specialty Chemicals.

Carbon black is preferred as a black pigment. Suitable black pigments include carbon blacks such as Pigment Black 7 (e.g. Carbon Black MA8™ from MITSUBISHI CHEMICAL), REGAL™ 400R, MOGUL™ L, ELFTEX™ 320 from CABOT Co., or Carbon Black FW18, Special Black 250, Special Black 350, Special Black 550, PRINTEX™ 25, PRINTEX™ 35, PRINTEX™ 55, PRINTEX™ 90, PRINTEX™ 150T from DEGUSSA. Additional examples of suitable pigments are disclosed in U.S. Pat. No. 5,389,133 (XEROX).

It is also possible to make mixtures of pigments. For example, in some applications a neutral black ink is preferred and can be obtained e.g. by mixing a black pigment and a cyan pigment into the ink. Also pigments may be combined to enlarge the colour gamut of an ink set. The application may also require one or more spot colours. Silver and gold are often desired colours for making a product more attractive by giving it an exclusive appearance.

Also non-organic pigments may be present in the inks. Suitable pigments are C.I. Pigment Metal 1, 2 and 3. Illustrative examples of the inorganic pigments include titanium oxide, barium sulphate, calcium carbonate, zinc oxide, lead sulphate, yellow lead, zinc yellow, red iron oxide (III), cadmium red, ultramarine blue, prussian blue, chromium oxide green, cobalt green, amber, titanium black and synthetic iron black. However, care should be taken to prevent migration and extraction of heavy metals in food application. In the preferred embodiment no pigments are used which contain a heavy metal selected from the group consisting of arsenic, lead, mercury and cadmium.

Pigment particles in inkjet ink should be sufficiently small to permit free flow of the ink through the inkjet-printing device, especially at the ejecting nozzles. It is also desirable to use small particles for maximum colour strength and to slow down sedimentation.

The numeric average pigment particle size is preferably between 0.050 and 1 µm, more preferably between 0.070 and 0.300 µm and particularly preferably between 0.080 and 0.200 µm. Most preferably, the numeric average pigment particle size is no larger than 0.150 µm. An average particle size smaller than 0.050 µm is less desirable for decreased light-fastness, but mainly also because very small pigment particles or individual pigment molecules thereof may still be extracted in food packaging applications.

The numeric average pigment particle size of pigment particles is best determined with a Brookhaven Instruments Particle Sizer BI90plus based upon the principle of dynamic light scattering. The ink is then diluted, for example, with ethyl acetate to a pigment concentration of 0.002 wt %. The measurement settings of the BI90plus are: 5 runs at 23° C., angle of 90°, wavelength of 635 nm and graphics=correction function.

In the case of a white curable ink, preferably a pigment with a refractive index greater than 1.60, preferably greater than 2.00, more preferably greater than 2.50 and most preferably greater than 2.60 is used. The white pigments may be employed singly or in combination.

Preferably titanium dioxide is used for the pigment with a refractive index greater than 1.60. Titanium oxide occurs in the crystalline forms of anatase type, rutile type and brookite type. The anatase type has a relatively low density and is easily ground into fine particles, while the rutile type has a relatively high refractive index, exhibiting a high covering power. Either one of these is usable in this invention. It is preferred to make the most possible use of characteristics and to make selections according to the use thereof. The use of the anatase type having a low density and a small particle size can achieve superior dispersion stability, ink storage stability and ejectability. At least two different crystalline forms may be used in combination. The combined use of the anatase type and the rutile type which exhibits a high coloring power can reduce the total amount of titanium oxide, leading to improved storage stability and ejection performance of ink.

For surface treatment of the titanium oxide, an aqueous treatment or a gas phase treatment is applied, and an alumina-silica treating agent is usually employed. Untreated-, alumina treated- or alumina-silica treated-titanium oxide are employable.

The numeric average particle diameter of the titanium oxide or other white pigments is preferably from 50 to 500 nm, more preferably from 150 to 400 nm, and most preferably from 200 to 350 nm. Sufficient hiding power cannot be obtained when the average diameter is less than 50 nm, and the storage ability and the jet-out suitability of the ink tend to be degraded when the average diameter exceeds 500 nm. The determination of the numeric average particle diameter is best performed by photon correlation spectroscopy at a wavelength of 633 nm with a 4 mW HeNe laser on a diluted sample of the pigmented inkjet ink. A suitable particle size analyzer used was a MALVERN™ nano-S available from Goffin-Meyvis. A sample can be, for example, be prepared by addition of one drop of ink to a cuvet containing 1.5 mL ethyl acetate and mixed until a homogenous sample was obtained. The measured particle size is the average value of 3 consecutive measurements consisting of 6 runs of 20 seconds.

Generally pigments are stabilized in the dispersion medium by dispersing agents, such as polymeric dispersants or surfactants. However, the surface of the pigments can be modified to obtain so-called "self-dispersible" or "self-dispersing" pigments, i.e. pigments that are dispersible in the dispersion medium without dispersants.

The pigment is preferably used in a pigment dispersion used for preparing inks in an amount of 10 to 40 wt %, more preferably of 15 to 30 wt % based on the total weight of the pigment dispersion. In a curable inkjet ink the pigment is preferably present in an amount of 0.1 to 20 wt %, preferably 1 to 10 wt % based on the total weight of the inkjet ink.

Dispersants

The dispersant is preferably a polymeric dispersant. Typical polymeric dispersants are copolymers of two monomers but may contain three, four, five or even more monomers. The properties of polymeric dispersants depend on both the nature of the monomers and their distribution in the polymer. Suitable copolymeric dispersants have the following polymer compositions:

statistically polymerized monomers (e.g. monomers A and B polymerized into ABBAABAB);

alternating polymerized monomers (e.g. monomers A and B polymerized into ABABABAB);

gradient (tapered) polymerized monomers (e.g. monomers A and B polymerized into AAABAABBABBB);

block copolymers (e.g. monomers A and B polymerized into AAAAABBBBBB) wherein the block length of each of the blocks (2, 3, 4, 5 or even more) is important for the dispersion capability of the polymeric dispersant;

graft copolymers (graft copolymers consist of a polymeric backbone with polymeric side chains attached to the backbone); and mixed forms of these polymers, e.g. blocky gradient copolymers.

Suitable polymeric dispersants are listed in the section on polymeric dispersants in EP 1790696 A (AGFA) incorporated herein as a specific reference.

The polymeric dispersant has preferably a polymerization degree DP between 5 and 1,000, more preferably between 10 and 500 and most preferably between 10 and 100.

The polymeric dispersant has preferably a number average molecular weight Mn between 500 and 30,000, more preferably between 1,500 and 10,000.

The polymeric dispersant has preferably a weight average molecular weight Mw smaller than 100,000, more preferably smaller than 50,000 and most preferably smaller than 30,000.

The polymeric dispersant has preferably a polydispersity PD smaller than 2, more preferably smaller than 1.75 and most preferably smaller than 1.5.

Commercial examples of polymeric dispersants are the following:

DISPERBYK™ dispersants available from BYK CHEMIE GMBH;

SOLSPERSE™ dispersants available from NOVEON;

TEGO™ DISPERS™ dispersants from DEGUSSA;

EDAPLAN™ dispersants from MÜNZING CHEMIE;

ETHACRYL™ dispersants from LYONDELL;

GANEX™ dispersants from ISP;

DISPEX™ and EFKA™ dispersants from CIBA SPECIALTY CHEMICALS INC;

DISPONER™ dispersants from DEUCHEM; and

JONCRYL™ dispersants from JOHNSON POLYMER.

Particularly preferred polymeric dispersants include SOL-SPERSE™ dispersants from NOVEON, EFKA™ dispersants from CIBA SPECIALTY CHEMICALS INC and DISPERBYK™ dispersants from BYK CHEMIE GMBH.

Particularly preferred dispersants for UV-curable pigmented dispersions are SOLSPERSE™ 32000, 35000 and 39000 dispersants from NOVEON.

The polymeric dispersant is preferably used in an amount of 2 to 600 wt %, more preferably 5 to 200 wt % based on the weight of the pigment.

Preparation of Radiation Curable Inks

The average particle size and distribution is an important feature for inkjet inks. The ink may be prepared by precipitating or milling the pigment in the dispersion medium in the presence of the dispersant.

Mixing apparatuses may include a pressure kneader, an open kneader, a planetary mixer, a dissolver, and a Dalton Universal Mixer. Suitable milling and dispersion apparatuses are a ball mill, a pearl mill, a colloid mill, a high-speed disperser, double rollers, a bead mill, a paint conditioner, and triple rollers. The dispersions may also be prepared using ultrasonic energy.

Many different types of materials may be used as milling media, such as glasses, ceramics, metals, and plastics. In a preferred embodiment, the grinding media can include particles, preferably substantially spherical in shape, e.g. beads consisting essentially of a polymeric resin or yttrium stabilized zirconium oxide beads.

In the process of mixing, milling and dispersion, each process is performed with cooling to prevent build up of heat, and for radiation curable inks as much as possible under light conditions in which actinic radiation has been substantially excluded.

The ink may contain more than one pigment, the ink may be prepared using separate dispersions for each pigment, or alternatively several pigments may be mixed and co-milled in preparing the dispersion.

The dispersion process can be carried out in a continuous, batch or semi-batch mode.

The preferred amounts and ratios of the ingredients of the mill grind will vary widely depending upon the specific materials and the intended applications. The contents of the milling mixture include the mill grind and the milling media. The mill grind includes pigment, polymeric dispersant and a liquid carrier. For inkjet inks, the pigment is usually present in the mill grind at 1 to 50 wt %, excluding the milling media. The weight ratio of pigment over polymeric dispersant is 20:1 to 1:2.

The milling time can vary widely and depends upon the pigment, selected mechanical device and residence conditions, the initial and desired final particle size, etc. In preferred embodiments of the present invention pigment dispersions with an average particle size of less than 100 nm may be prepared.

After milling is completed, the milling media is separated from the milled particulate product (in either a dry or liquid dispersion form) using conventional separation techniques, such as by filtration, sieving through a mesh screen, and the like. Often the sieve is built into the mill, e.g. for a bead mill. The milled pigment concentrate is preferably separated from the milling media by filtration.

In general it is desirable to make the inks in the form of a concentrated mill grind, which is subsequently diluted to the appropriate concentration for use in the printing system. This technique permits preparation of a greater quantity of pigmented ink from the equipment. By dilution, the ink is adjusted to the desired viscosity, surface tension, colour, hue, saturation density, and print area coverage for the particular application.

Inkjet Printing Methods

The inkjet printing method according to a preferred embodiment of the present invention includes the steps of:
a) providing a radiation curable composition according to a preferred embodiment of the present invention; and
b) at least partially curing the radiation curable composition.

In a preferred embodiment of the inkjet printing method according to the present invention, the radiation curable composition is applied to a substrate by inkjet printing or by flexographic printing. For example, the radiation curable composition is applied as a primer on a substrate by flexographic printing and at least partially cured, and then a solvent inkjet ink or radiation curable inkjet ink is printed on the at least partially cured primer.

In one embodiment of the inkjet printing method, the applied layer is a white primer, preferably containing a titanium dioxide pigment. White primers can be advantageously used, for example, on transparent substrates to enhance the contrast and the vividness of colour inks. White curable inks are then either used for so-called "surface printing" or "backing printing" to form a reflection image on a transparent substrate. In surface printing, a white background is formed on a transparent substrate using a white ink and further thereon, a color image is printed, where after the formed final image is viewed from the printed face. In so-called backing printing, a color image is formed on a transparent substrate using color inks and then a white ink is applied onto the color inks, and the final formed image is observed through the transparent substrate. In a preferred embodiment a colour inkjet ink is jetted on partially cured white inkjet ink. If the white ink is only partially cured, an improved wettability of the colour ink on the white ink layer is observed. Partially curing immobilizes the ink on the substrate surface. A quick test to verify that the white inkjet ink is partially cured can be done by rubbing a finger or a cloth across the printed surface, whereby it is observed that ink can be smeared or smudged on the surface.

In another preferred embodiment of the inkjet printing method, the applied layer is a colourless layer. This layer can be present as a primer, for example, for improving the adhesion of the image, or as an outermost layer, for example, for improving the glossiness of the image.

The above layers are preferably applied by a printing technique selected from the group consisting of inkjet printing, flexographic printing, offset printing and screen printing.

Alternatively, above layers are applied by a coating technique selected from the group consisting of dip coating, knife coating, extrusion coating, spin coating, slide hopper coating and curtain coating.

Inkjet Printing Device

Curable liquids and inks according to preferred embodiments of to the present invention may be jetted by one or more print heads ejecting small droplets of ink in a controlled manner through nozzles onto an ink-receiver surface, which is moving relative to the print head(s).

A preferred print head for the inkjet printing system is a piezoelectric head. Piezoelectric inkjet printing is based on the movement of a piezoelectric ceramic transducer when a voltage is applied thereto. The application of a voltage changes the shape of the piezoelectric ceramic transducer in the print head creating a void, which is then filled with ink. When the voltage is again removed, the ceramic expands to its original shape, ejecting a drop of ink from the print head. However the inkjet printing method of the present invention is not restricted to piezoelectric inkjet printing. Other inkjet print heads can be used and include various types, such as a continuous type and thermal, electrostatic and acoustic drop on demand type.

At high printing speeds, the inks must be ejected readily from the print heads, which puts a number of constraints on the physical properties of the ink, e.g. a low viscosity at the jetting temperature, which may vary from 25° C. to 110° C., a surface energy such that the print head nozzle can form the necessary small droplets, a homogenous ink capable of rapid conversion to a dry printed area, . . . .

The inkjet print head normally scans back and forth in a transversal direction across the moving ink-receiver surface. Often the inkjet print head does not print on the way back. Bi-directional printing is preferred for obtaining a high areal throughput. Another preferred printing method is by a "single pass printing process", which can be performed by using page wide inkjet print heads or multiple staggered inkjet print heads which cover the entire width of the ink-receiver surface. In a single pass printing process the inkjet print heads usually remain stationary and the ink-receiver surface is transported under the inkjet print heads.

Curing Device

Curable liquids and inks according to preferred embodiments of the present invention can be cured by exposing them to actinic radiation, preferably by ultraviolet radiation.

The curing device may be arranged in combination with the print head of the inkjet printer, travelling therewith so that the curable liquid is exposed to curing radiation very shortly after been jetted.

In such an arrangement it can be difficult to provide a small enough radiation source connected to and travelling with the print head. Therefore, a static fixed radiation source may be employed, e.g. a source of curing UV-light, connected to the radiation source by means of a flexible radiation conductor such as a fibre optic bundle or an internally reflective flexible tube.

Alternatively, the actinic radiation may be supplied from a fixed source to the radiation head by an arrangement of mirrors including a mirror upon the radiation head.

The source of radiation arranged not to move with the print head, may also be an elongated radiation source extending transversely across the ink-receiver surface to be cured and adjacent the transversal path of the print head so that the subsequent rows of images formed by the print head are passed, stepwise or continually, beneath that radiation source.

Any ultraviolet light source, as long as part of the emitted light can be absorbed by the photo-initiator or photo-initiator system, may be employed as a radiation source, such as, a high or low pressure mercury lamp, a cold cathode tube, a black light, an ultraviolet LED, an ultraviolet laser, and a flash light. Of these, the preferred source is one exhibiting a relatively long wavelength UV-contribution having a dominant wavelength of 300-400 nm. Specifically, a UV-A light source is preferred due to the reduced light scattering therewith resulting in more efficient interior curing.

UV radiation is generally classed as UV-A, UV-B, and UV-C as follows:
 UV-A: 400 nm to 320 nm
 UV-B: 320 nm to 290 nm
 UV-C: 290 nm to 100 nm.

Furthermore, it is possible to cure the image using, consecutively or simultaneously, two light sources of differing wavelength or illuminance. For example, the first UV-source can be selected to be rich in UV-C, in particular in the range of 260 nm-200 nm. The second UV-source can then be rich in UV-A, e.g. a gallium-doped lamp, or a different lamp high in both UV-A and UV-B. The use of two UV-sources has been found to have advantages e.g. a fast curing speed and a high curing degree.

For facilitating curing, the inkjet printer often includes one or more oxygen depletion units. The oxygen depletion units place a blanket of nitrogen or other relatively inert gas (e.g. $CO_2$), with adjustable position and adjustable inert gas concentration, in order to reduce the oxygen concentration in the curing environment. Residual oxygen levels are usually maintained as low as 200 ppm, but are generally in the range of 200 ppm to 1,200 ppm.

EXAMPLES

Materials

All materials used in the following examples were readily available from standard sources such as Aldrich Chemical Co. (Belgium) and Acros (Belgium) unless otherwise specified. The water used was deionized water.

DPGDA is dipropyleneglycoldiacrylate from SARTOMER.

VEEA is 2-(vinylethoxy)ethyl acrylate, a difunctional monomer available from NIPPON SHOKUBAI, Japan.

TMPTA is trimethylolpropane triacrylate available as SARTOMER™ SR351 from SARTOMER.

M600 is dipentaerythritol hexaacrylate and an abbreviation for MIRAMER™ M600 available from RAHN AG.

2-Hydroxythioxanthen-9-one was prepared according to the example 1 of GB 2108487 (SERICOL).

IRGACURE™ 127 is 2-hydroxy-1-{4-[4-(2-hydroxy-2-methyl-propionyl)-benzyl]-phenyl}-2-methyl-propan-1-one, a photoinitiator available from CIBA SPECIALTY CHEMICALS.

COMPINI-1 is a comparative initiator which was prepared according to Top et al., Journal of Organometallic Chemistry 643-644, 350-356 (2002).

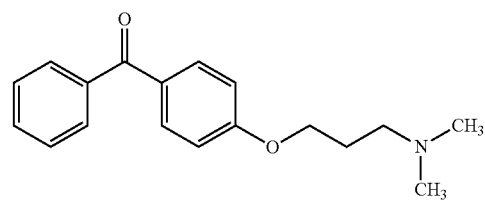 [SMILES: CN(C)CCCOc1ccc(C(=O)c2ccccc2)cc1]

COMPINI-1.

COMPINI-2 is a comparative initiator represented by the following formula:

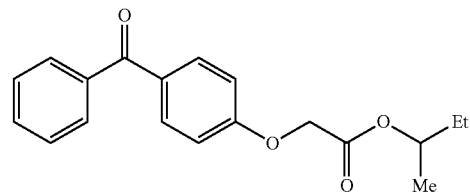 [SMILES: CCC(C)OC(=O)COc1ccc(C(=O)c2ccccc2)cc1]

COMPINI-2.
COMPINI-2 was synthesized as follows:

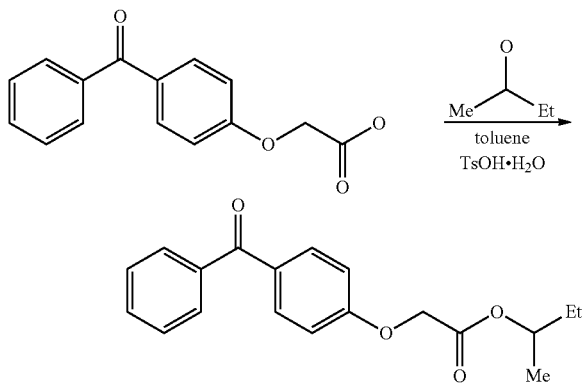

(4-benzoylphenoxy)-acetic acid was prepared according to Chen et al., Macromolecular Chemistry and Physics (2007), 208(15), 1694-1706. 25.6 g (0.10 mol) (4-benzoylphenoxy)-acetic acid was dissolved in 100 mL toluene and 30 mL dimethyl acetamide. 14.8 g (0.20 mol) sec. butanol and 28 g (0.15 mol) p.-toluene sulfonic acid were added. The reaction mixture was refluxed under azeotropical removal of water. 250 mL ethyl acetate was added and the mixture was extracted with 200 mL 1 N NaOH. The organic fraction was dried over $MgSO_4$ and the solvent was removed under reduced pressure. COMPINI-2 was isolated as a white crystalline compound. 29.8 g (95%) of COMPINI-2 was isolated.

COMPCOINI-1 is a comparative co-initiator represented by the following formula:

COMPCOINI-1

COMPCOINI-1 was synthesized as follows:

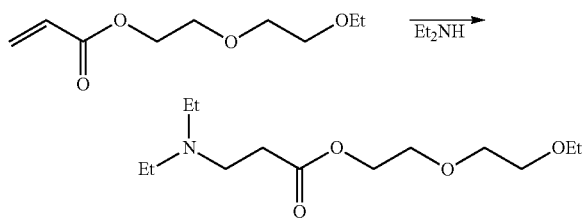

7.53 g (40 mmol) of 2-(2-ethoxyethoxy)ethyl acrylate was heated to 50° C. 2.93 g (40 mmol) diethyl amine was added dropwise and the reaction was allowed to continue for four hours at 50° C. An additional 0.145 g (2 mmol) diethyl amine was added and the reaction was allowed to continue for an additional three hours at 50° C. The reaction mixture was allowed to cool down to room temperature. GC analysis revealed a complete conversion of the acrylate. COMPCOINI-1 was used without further purification.

TEGO™ Rad 2100 is a silicone polyether acrylate surfactant available from DEGUSSA.

Surfactant A is a solution of 1 wt % TEGO™ Rad 2100 in VEEA.

SPECIAL BLACK™ 550 is a carbon black pigment with a BET of 110 $m^2$/g available from DEGUSSA.

HOSTAPERM™ Blue P-BFS is a cyan pigment (C.I. Pigment Blue 15:4) available from CLARIANT.

CINQUASIA™ Magenta RT-355-D is a quinacridone pigment from CIBA SPECIALTY CHEMICALS.

PY150 is an abbreviation used for Yellow Pigment E4GN-GT, a C.I.

Pigment Yellow 150 pigment from LANXESS.

GENORAD™ 16 is a polymerization inhibitor from RAHN AG. S35000 is an abbreviation for SOLSPERSE™ 35000, a polyethyleneimine-polyester hyperdispersant from NOVEON.

PET100 is a 100 μm unsubbed PET substrate with on the backside an antiblocking layer with antistatic properties available from AGFA-GEVAERT as P100C PLAIN/ABAS.

Measurement

1. TDE-Level

The TDE-level represents the amount of volatile extractables by thermal desorption. The amount of volatile extractables is determined on fully cured coatings by direct thermal desorption method, i.e. without sample preparation. The fully cured coating on a PET100 substrate having a backing layer was analysed with a GERSTEL™ TDS2 ThermoDesorption System from Gerstel Gmbh & Co. KG using as operation conditions: 1.54 $cm^2$ of the cured coating was analyzed during 10 minutes at 150° C. with on-line GC evaluation of peak intensity for the desorbed components. The oven program was set to 40° C. for 30 seconds, followed by a temperature increase at a rate of 15° C./minute until 300° C., and keeping the sample at 300° C. for 5 minutes. The chromatographic column was a Db1 column from J&W (30 m×0.32 mm, 1 mm film thickness); the carrier gas was He at a flow rate of 2 mL/min. The desorbed compounds were trapped on Tenax TA at −60° C.

The back coating on the PET100 substrate contained volatile compounds, including NMP. The amount of NMP detected was used as an internal standard to calculate the amount of volatile compounds from the cured coating expressed in ppm (mg extractable compound per g of curable liquid). The amount of volatile compounds of the cured coating is obtained by subtraction of the amount of volatile compounds of the PET100 substrate from the total amount of volatile compounds of cured coating and PET100 substrate. This amount is very much depending upon the composition of the curable liquid. The evaluation scale used for the examples is given by Table 3.

TABLE 3

| Total amount of desorbed components from the cured coating | Evaluation |
|---|---|
| >5,000 ppm | bad |
| >3,000 ppm | poor |
| 1,000-3,000 ppm | acceptable |
| <1,000 ppm | good |
| <500 ppm | very good |

2. Curing Degree

The curing degree is tested on a coating immediately after curing with UV light. The cured coating is rubbed with a Qtip. When the surface is not damaged, the coating is fully cured. When some of the cured coating can be damaged, the coating is only partly cured. When the whole cured coating is damaged, the coating is not cured.

3. Curing Speed

The curing speed was defined as the percentage of the maximum output of the lamp needed to cure the samples. The lower the number the higher curing speed. A sample was considered as fully cured at the moment scratching with a Q-tip caused no visual damage.

A percentage of more then 100% of the maximum output of the lamp means that the speed of the conveyer belt had to be reduced to get the sample fully cured at the maximum output of the lamp. The higher the percentage, the more the belt had to be slowed down. A curing speed of 160% means a belt speed of 12.5 m/min at the maximum output of the lamp. A percentage between 150% and 200% is considered as at the edge of practical use. A percentage above 200% is considered out of the range for practical use and no higher percentages are measured.

4. Viscosity

The viscosity of the formulations was measured using a Brookfield DV-II+ viscometer at 25° C. at 3 rotations per minute (RPM) using a CPE 40 spindle. A viscosity of less than 50 mPa·s was regarded to be suitable for inkjet printing.

Example 1

This example illustrates the synthesis of several multifunctional photoinitiators according to a preferred embodiment of the present invention.

The Synthesis of INI-1

Synthesis of 4-[(3-methylamino)propoxy]benzophenone

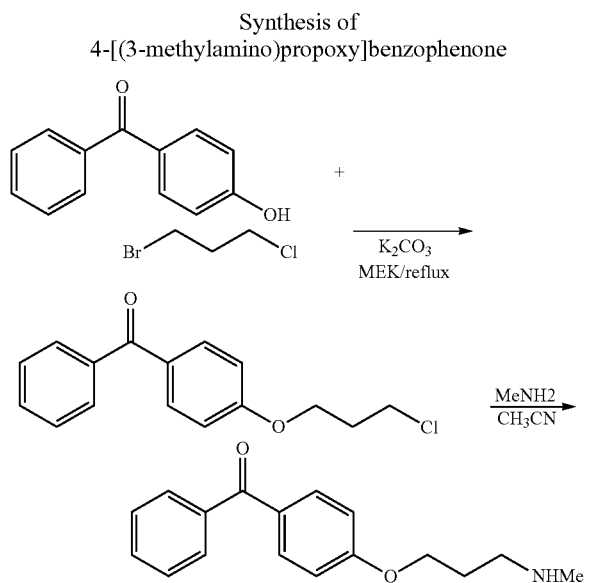

253.7 g (1.27 mol) 4-hydroxybenzophenone was dissolved in 2.56 L 2-butanone. 884.5 g (6.3 mol) potassium carbonate and 201.5 g (1.27 mol) 1-bromo-3-chloro-propane were added. The mixture was refluxed for 16 hours. The mixture was allowed to cool down to room temperature and the inorganic salts were removed by filtration. The solvent was removed under reduced pressure. The residue was treated with 250 mL acetone and 600 mL isopropyl acetate. The residue partially solidified. The solvent was removed and the residue was treated with 1.5 L water. The crude 4-(3-chloropropoxy)benzophenone crystallized from the medium, was isolated by filtration and dried. 228 g of the crude 4-(3-chloropropoxy)benzophenone was isolated.

109.9 g (0.4 mol) of the crude 4-(3-chloropropoxy)benzophenone was dissolved in 550 mL acetonitrile. 310 g (4 mol) of a 40% solution of methyl amine in water was added and the mixture was heated to 60° C. for 2 hours. The undissolved residue in the reaction mixture was removed by filtration and an additional 155 g (2 mol) of a 40% solution of methyl amine in water was added. The reaction was allowed to continue for 4 hours at 60° C. The reaction was allowed to cool down to room temperature and the solvent was removed under reduced pressure. The residue was dissolved in 1 L water and the pH was adjusted to 1.4 using a 6NHCl-solution. The mixture was stirred for 2 hours at 40° C. and the precipitated product was isolated by filtration. The residue was treated with 500 mL methylene chloride, isolated by filtration and dried. The hydrochloric acid salt was dissolved in 500 mL water and the pH was adjusted to 12 using a 10 N NaOH solution. The mixture was extracted with 500 mL methylene chloride. The organic fraction was dried over MgSO$_4$ and the solvent was removed under reduced pressure. The oily residue crystallized upon standing. 60 g (56%) of 4-[(3-methylamino)propoxy]benzophenone was isolated.

Synthesis of 3-{[3-(4-benzoylphenoxy)-propyl]-methyl-amino}-propionic acid

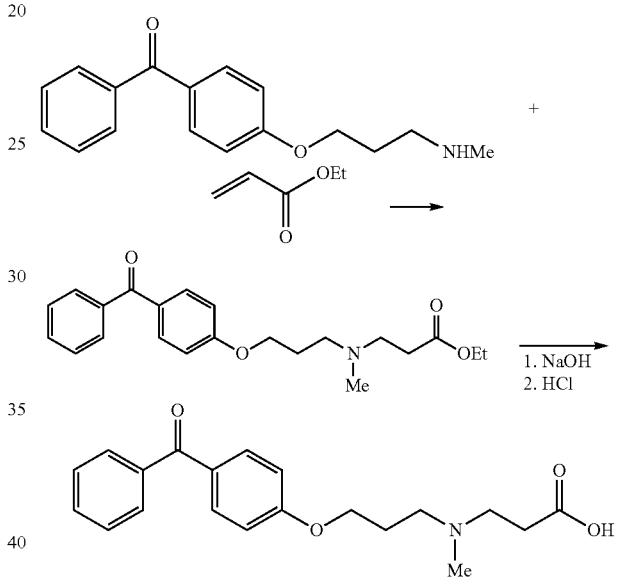

8.1 g (30 mmol) 4-[(3-methylamino)propoxy]benzophenone was dissolved in 150 mL methylene chloride. 4.1 g (40 mmol) ethyl acrylate was added and the reaction was allowed to continue for 18 hours at room temperature. The solvent was evaporated under reduced pressure and the crude 3-{[3-(4-benzoylphenoxy)-propyl]-methyl-amino}-propionic acid ethyl ester was dissolved in 70 mL ethanol. 8 mL of a 5 N NaOH solution was added and the reaction was allowed to continue for 1 hour at room temperature. The reaction mixture was acidified with a 6 N HCl solution and a small amount of precipitated contaminants were removed by filtration. The solvent was removed under reduced pressure. The oily residue was treated with 100 mL t.butyl-methyl-ether. The crude 3-{[3-(4-benzoylphenoxy)-propyl]-methyl-amino}-propionic acid was isolated by filtration and redissolved in 100 mL 1-methoxy-2-propanol. The undissolved sodium chloride was removed by filtration and the solvent was evaporated under reduced pressure. 3-{[3-(4-benzoylphenoxy)-propyl]-methyl-amino}-propionic acid was purified by preparative column chromatography on a Prochrom LC80 column, using a gradient elution from 10/90 methanol/water to 73/27 methanol/water on Kromasil 100A 10 m as silica and at a flow rate of 150 mL/min. 2.8 g (26%) of 3-{[3-(4-benzoylphenoxy)-propyl]-methyl-amino}-propionic acid was isolated as a white crystalline solid. According to $^1$H-NMR analysis 3-{[3-(4-benzoylphenoxy)-propyl]-methyl-amino}-propionic acid had a purity of 98%.

Synthesis of Photoinitiator INI-1

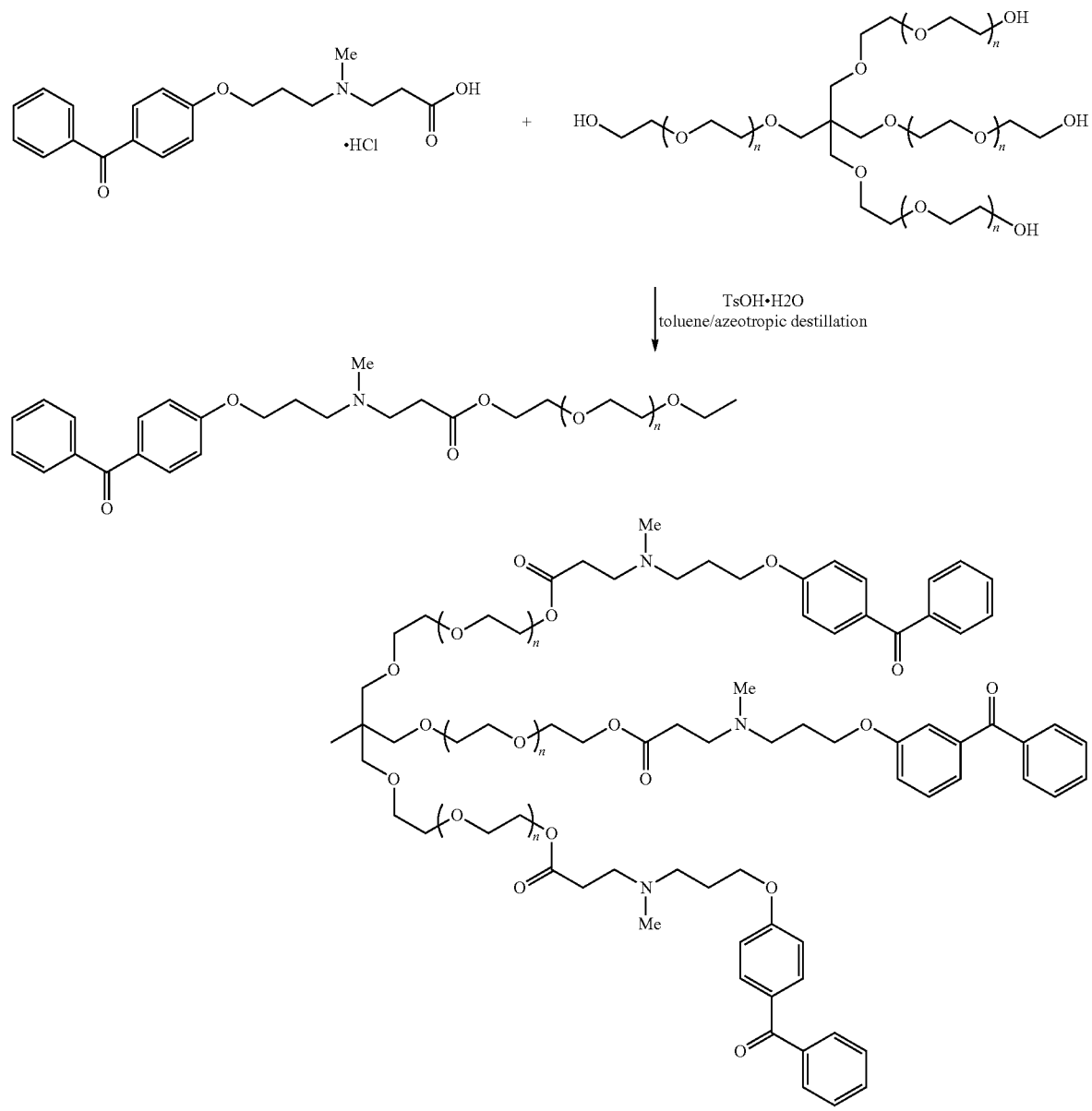

A mixture of 3-{[3-(4-benzoylphenoxy)-propyl]-methyl-amino}-propionic acid (2.5 g, 0.0073 mol), pentaerythritol ethoxylate (15/4 EO/OH), Mn~797 (1.5 g, 0.001825 mol) and p-toluenesulfonic acid monohydrate (1.9 g, 0.01 mol) in toluene (140 mL) was heated at reflux for 3 hours while water was removed by azeotropic distillation. The reaction mixture was cooled to room temperature and the toluene phase was decanted off. The residual oil was brought in ethyl acetate and extracted with a mixture of an aqueous solution of sodium carbonate (1M) and distilled water (1/3). The organic layer was isolated and dried over $MgSO_4$. Evaporation of the solvent provided 3.1 g of a yellow oil. The $^1$H-NMR analysis showed an end group conversion of 80%.

The Synthesis of INI-2

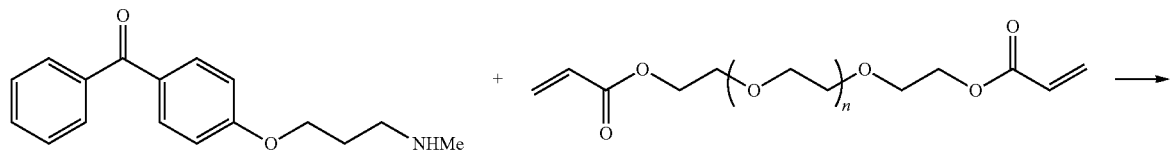

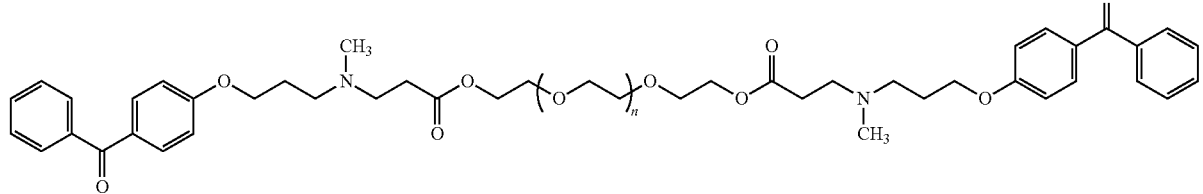

where n=3 on average

A solution of poly(ethylene glycol)diacrylate, Mn~258 (5.41 g, 0.021 mol) and 2,6-di-tert-butyl-4-methylphenol (0.04 g, 0.0001 mol) in 55 mL ethyl acetate was heated at 75° C. 4-[(3-methylamino)propoxy]benzophenone (10.77 g, 0.042 mol) was added at 75° C. The mixture was stirred for about 18 hours. The reaction mixture was cooled to room temperature and the solvent was evaporated under reduced pressure.

The product was purified on a Prochrom LC80 Column using dichloromethane/methanol (95/5) as eluent, to afford 7.0 g of a clear oil.

The Synthesis of INI-3

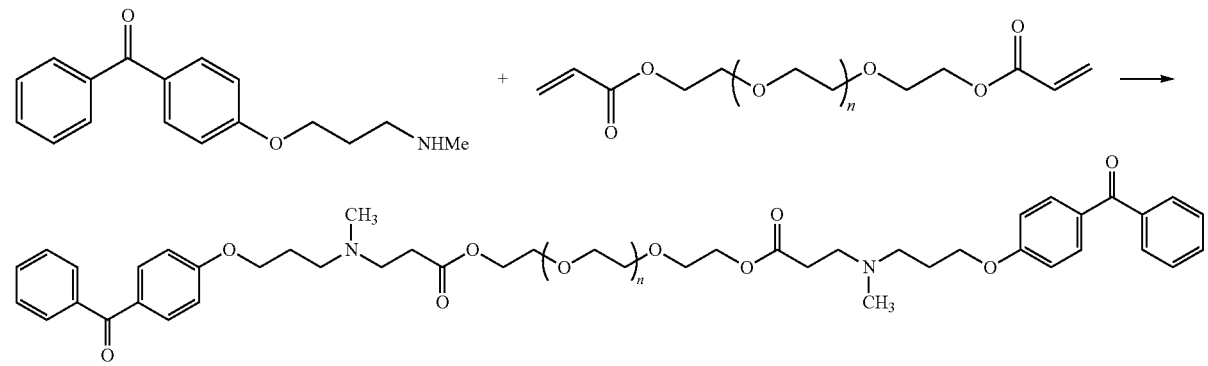

where n=11 on average

A solution of poly(ethylene glycol)diacrylate, Mn~575 (18.46 g, 0.0321 mol) and 2,6-di-tert-butyl-4-methylphenol (0.07 g, 0.0003 mol) in 85 mL ethyl acetate was heated at 75° C. 4-[(3-methylamino)propoxy]benzophenone (16.16 g, 0.06 mol) was added at 75° C.

The mixture was stirred for about 24 hours. The reaction mixture was filtered at a temperature of 65° C. to remove the formed precipitate. Evaporation of the solvent provided 35.37 g of a yellow oil.

The Synthesis of INI-4

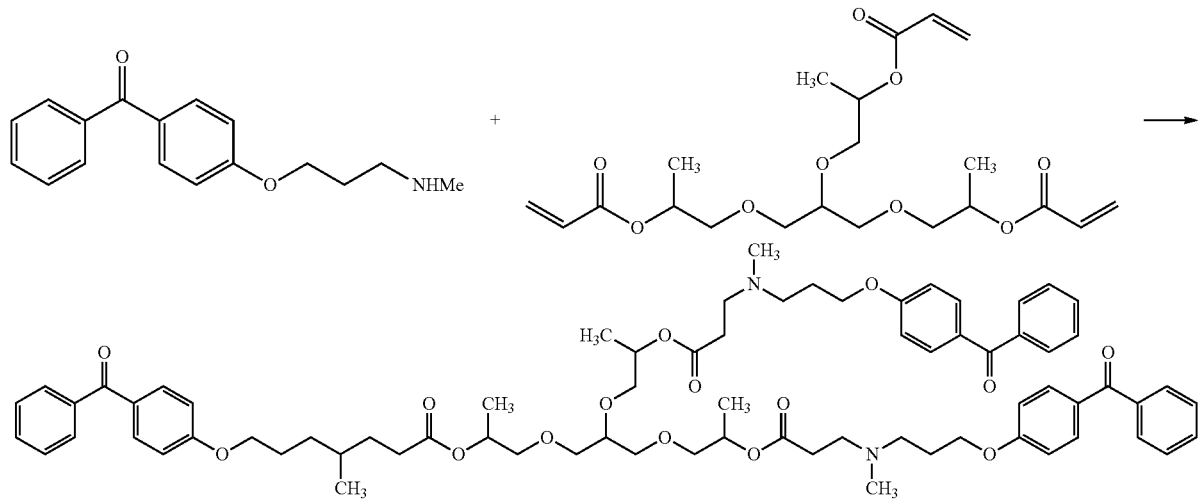

A solution of propoxylated (3) glyceryl triacrylate (18.0 g, 0.042 mol) and 2,6-di-tert-butyl-4-methylphenol (0.09 g, 0.00042 mol) in 35 mL ethyl acetate was heated at 70° C. 4-(3-methylamino-propoxy)-benzophenone (16.2 g, 0.06 mol) was added at 70° C.

The mixture was stirred for about 48 hours. The solvent was removed under reduced pressure and dried under vacuum at 35° C. to provide 35 g of a yellow oil.

The Synthesis of INI-6

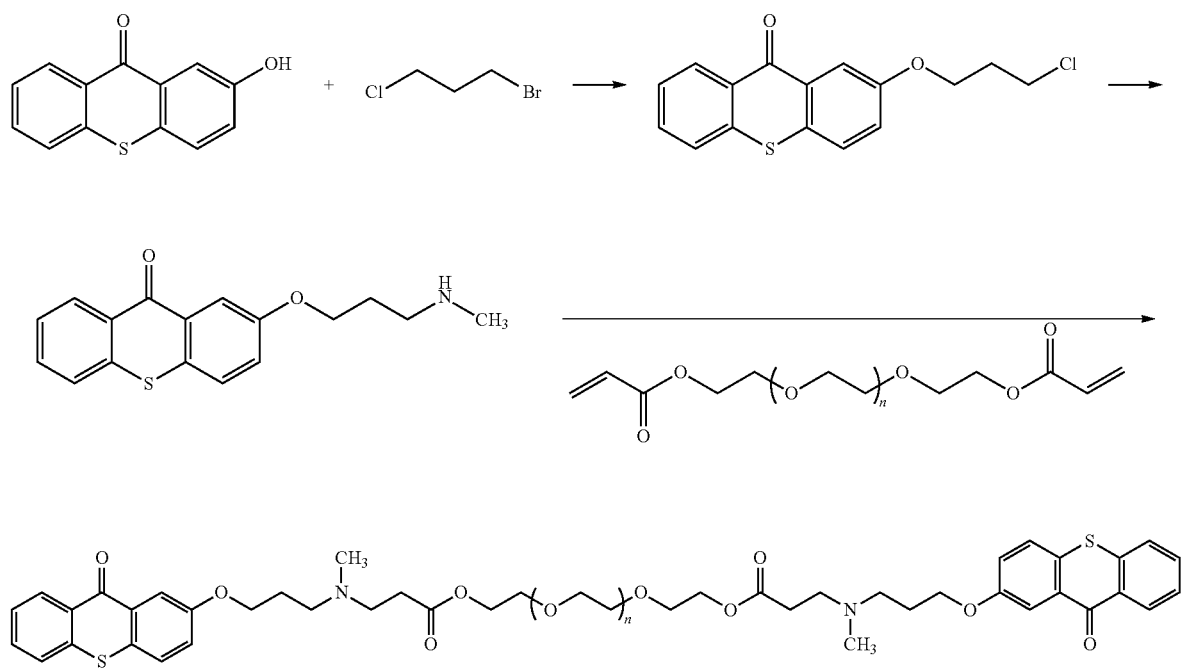

30 g (0.13 mol) 2-hydroxythioxanthen-9-one was suspended in 350 mL acetone. 61.6 g (0.39 mol) 1-bromo-3-chloro-propane and 62.8 g (0.46 mol) potassium carbonate were added. The mixture was refluxed for 6 hours. The mixture was allowed to cool down to room temperature. The precipitated salts were removed by filtration and the solvent was evaporated under reduced pressure. The residue was suspended in a mixture of 300 mL ethyl acetate and 200 mL water. The precipitated residue was isolated by filtration and redissolved in a mixture of 100 mL methylene chloride and 50 mL water. Both the ethyl acetate fraction and methylene chloride fraction were isolated, pooled and dried over MgSO$_4$. The solvent was removed under reduced pressure and 2-(3-chloropropoxy)-9H-thioxanthen-9-one was purified by preparative column chromatography on a Merck SVP D40 column, using a gradient elution from methylene chloride/hexane 30/70 to methylene chloride/hexane 50/50 at a flow rate of 40 mL per minute. 26.5 g of 2-(3-chloropropoxy)-9H-thioxanthen-9-one was isolated.

26 g (85 mmol) 2-(3-chloropropoxy)-9H-thioxanthen-9-one is suspended in 140 mL acetonitrile. 66 g (73.2 mL, 0.85 mol) of a 40% solution of methyl amine in water was added and the mixture was heated to 60° C. After four hours, 1.3 g (8.5 mmol) sodium iodide and 20 mL of a 40% solution of methyl amine in water were added and the reaction was allowed to continue for 16 hours at 60° C. The precipitated compounds were isolated by filtration and washed three times with 100 mL acetonitrile. The pooled acetonitrile fractions were evaporated under reduced pressure. The crude 2-(3-methylaminopropoxy)thioxanthen-9-one was crystallized from 200 mL hexane, isolated by filtration and dried. 19 g of 2-(3-methylaminopropoxy)thioxanthen-9-one was isolated. 2-(3-methylaminopropoxy)thioxanthen-9-one was further purified by preparative column chromatography on a Prochrom LC80 column, using Kromasil C18 100A 10 mm as silica and methanol/1M ammonium acetate 68/32 as eluent at a flow rate of 150 mL per minute.

2.4 g (6.9 mmol) 2-(3-methylaminopropoxy)thioxanthen-9-one and 2 g (3.4 mmol) polyethylene glycol diacrylate ($M_n$ @ 575) were dissolved in 80 mL methylene chloride. The reaction mixture was heated to reflux and the reaction was allowed to continue for 18 hours. The reaction was allowed to cool down to room temperature. The precipitated compounds were removed by filtration and the solvent was evaporated under reduced pressure. The crude INI-6 was purified by preparative size exclusion chromatography on a Plgel 5 mm 500 A (500-30000) column supplied by Polymer Laboratories Ltd., using tetrahydrofuran as eluent at a flow rate of 10 mL per minute. 1.6 g of INI-6 was isolated.

The Synthesis of INI-7

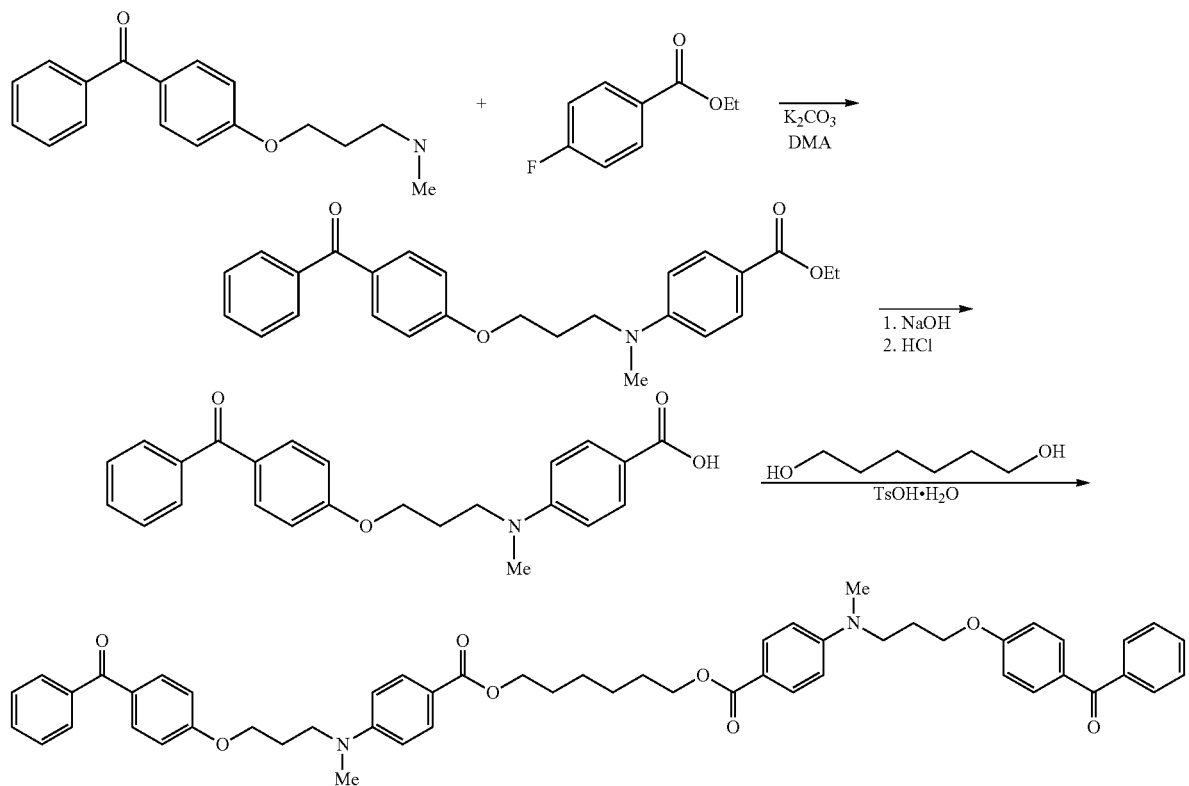

10.8 g (40 mmol) 4-[(3-methylamino)propoxy]benzophenone was dissolved in 55 mL dimethyl acetamide. 13.5 g (80 mmol) 4-fluoro-benzoic acid ethyl ester and 11.1 g (80 mmol) potassium carbonate were added. The reaction mixture was heated to 143° C. and the reaction was allowed to continue for 16 hours at 143° C. The reaction mixture was allowed to cool down to room temperature. 200 mL water was added and the mixture was extracted twice with 200 mL t.butyl methyl ether and once with 200 mL ethyl acetate. The pooled organic fractions were dried over $MgSO_4$. The solvent was removed under reduced pressure and the crude 4-dialkylamino benzoic acid ethyl ester derivative was purified by preparative column chromatography on a Prochrom LC80 column, using Kromasil Si 60 Å 10 m as silica and ethyl acetate/methylene chloride 3/97 as eluent at a flow rate of 150 mL per minute. 5.59 g of the intermediate 4-dialkylamino benzoic acid ethyl ester was isolated.

5.6 g (13.4 mmol) of the intermediate 4-dialkylamino benzoic acid ethyl ester was dissolved in 150 mL ethanol. 3.15 mL 10 N NaOH was added and the reaction mixture was refluxed for 20 hours. The solvent was removed under reduced pressure and the residue was dissolved in water. The solution was acidified to pH=1.6, using a 6 N HCl solution. The intermediate carboxylic acid precipitated from the medium, was isolated by filtration and redissolved in a methylene chloride acetone mixture. The solution was dried over $MgSO_4$ and evaporated under reduced pressure. 4.4 g of the intermediate carboxylic acid was isolated.

0.3 g (2.85 mmol) 1,6-hexane diol and 1.6 g (8.4 mmol) p. toluene sulfonic acid monohydrate were added to a suspension of 2.2 g (5.7 mmol) of the intermediate carboxylic acid in 100 mL toluene. The mixture was refluxed for 5 hours under azeotropical removal of water. The mixture was allowed to cool down to room temperature. 100 mL ethyl acetate was added and the mixture was extracted with 100 mL water. The organic fraction was dried over $MgSO_4$. The solvent was removed under reduced pressure and the crude INI-7 was purified by preparative column chromatography on a SVP D40 Merck Np column, using a gradient elution from methylene chloride to methylene chloride/ethyl acetate 90/10 at a flow rate of 50 mL/min. 0.65 g of INI-7 was isolated.

The Synthesis of INI-10, INI-11 and INI-12

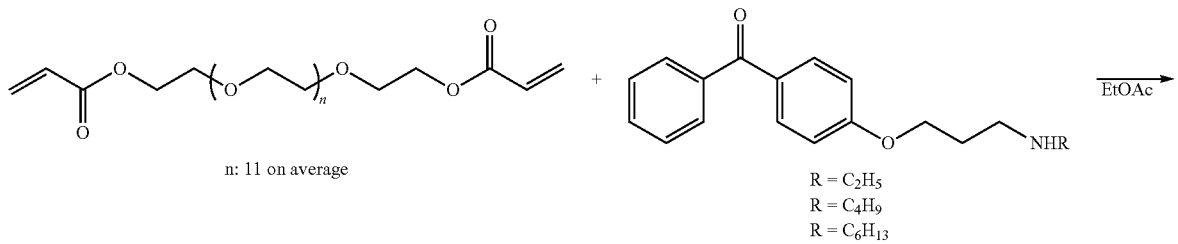

n: 11 on average $R = C_2H_5$
$R = C_4H_9$
$R = C_6H_{13}$

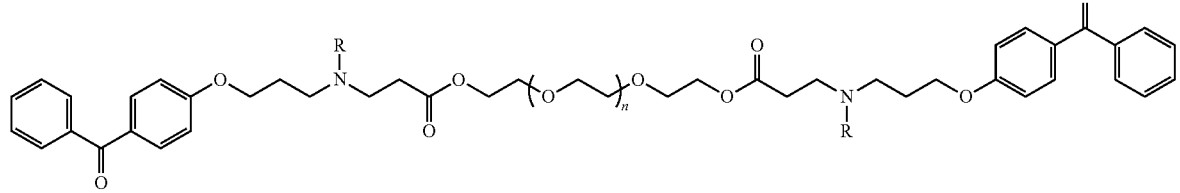

R = C$_2$H$_5$: INI-10
R = C$_4$H$_9$: INI-11
R = C$_6$H$_{13}$: INI-12

6 mmol of the appropriate benzophenone and 0.07 g (0.3 mmol) of 2,6-di-tert-butyl-4-methylfenol was dissolved in 10 mL ethylacetate. 1.73 g (3 mmol) of polyethylene glycol 600 diacrylate was dissolved in 5 mL ethylacetate and was added to the reaction mixture. After the addition of polyethylene glycol 600 diacrylate, the mixture was stirred for 5 h at 76° C. Finally the solvent was evaporated to afford a brown oil.

Synthesis of
4-[(3-alkylamino)propoxy]benzophenones

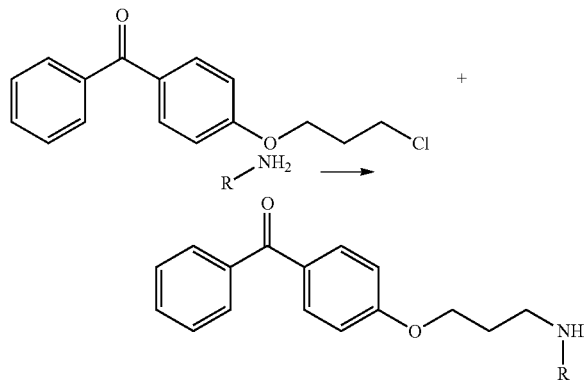

R=Et 25 g (91 mmol) 4-(3-chloropropoxy)benzophenone was dissolved in 300 mL acetonitrile. 82 g (1.26 mol) of a 70% of ethyl amine solution in water was added and the reaction mixture was heated to 70° C. The reaction was allowed to continue for 16 hours at 70° C. The solvent was evaporated under reduced pressure and the residue was treated with 100 mL water. The mixture was acidified to pH=1 and the precipitated products were isolated by filtration. The precipitated product was treated with a mixture of 200 mL ethyl acetate and 500 mL water. The aqueous fraction was isolated and the pH was adjusted to 12 using a 5 N NaOH solution. The mixture was extracted twice with 200 mL ethyl acetate. The organic fraction was dried over MgSO$_4$ and the solvent was evaporated under reduced pressure. 12.5 g of 4-[(3-ethylamino)propoxy]benzophenone was isolated.

R=Bu 10 g (36 mmol) 4-(3-chloropropoxy)benzophenone was dissolved in 100 mL acetonitrile. 26.3 g (0.36 mol) n.-butyl amine was added and the mixture was heated to 70° C. for 30 hours. The solvent was evaporated under reduced pressure and the residue was treated with 500 mL water. The pH was adjusted to pH=1. The mixture was stirred for one hour at 40° C. The mixture was cooled to 10° C. and the precipitated compounds were isolated by filtration. The precipitate was treated with 200 mL water and the pH was adjusted to 12, using a 1 N NaOH-solution. The mixture was extracted with 200 mL methylene chloride. The organic fraction was dried over MgSO$_4$ and evaporated under reduced pressure. The crude 4-[(3-butylamino)propoxy]benzophenone was purified by preparative column chromatography on a SVP D40 Merck-Np column, using a gradient elution from methylene chloride to methanol at a flow rate of 40 mL per minute. 4.4 g of 4-[(3-butylamino)propoxy]benzophenone was isolated.

R=C$_6$H$_{13}$ 10 g (36 mmol) 4-(3-chloropropoxy)benzophenone was dissolved in 100 mL acetonitrile. 36.4 g (0.36 mol) n.-hexyl amine was added and the mixture was heated to 70° C. for 20 hours. The solvent was evaporated under reduced pressure. The oily residue was treated with 500 mL water. The mixture was acidified to pH=1 and stirred for 16 hours at room temperature. The precipitated compounds were isolated by filtration and washed with 200 mL 1 N HCl. The precipitate was treated with 200 mL 1 N NaOH. The mixture was extracted with 200 mL methylene chloride. The organic fraction was dried over MgSO$_4$ and the solvent was evaporated under reduced pressure. The crude 4-[(3-hexylamino)propoxy]benzophenone was purified by preparative column chromatography on a Prochrom LC80 column, using Kromasil Si 60A 10 mm as silica and a gradient elution from methylene chloride to methylene chloride/methanol 68/32 at a flow rate of 150 mL per minute. 3.9 g of 4-[(3-hexylamino)propoxy]benzophenone was isolated.

The Synthesis of INI-17

Synthesis of poly(ethylene glycol) (200) ditosylate

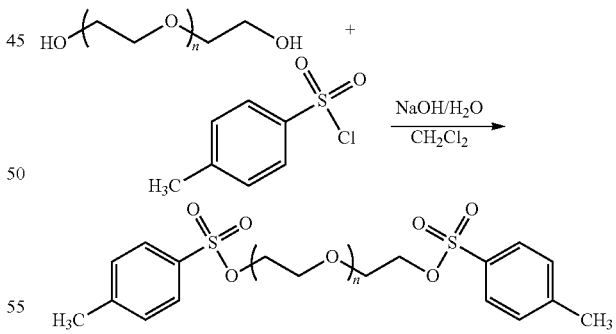

500 g (2.5 mol) poly(ethylene glycol) (200) was dissolved in 1 L methylene chloride. 950 g (5 mol) tosyl chloride was added and the reaction mixture was cooled to 0° C. A solution of 216 g (5.4 mol) sodium hydroxide in 216 mL water was added dropwise, while the temperature was kept below 5° C. The reaction was allowed to continue for 60 hours at room temperature. One liter water was added and the organic fraction was isolated. The organic fraction was washed twice with one liter water, dried over Na$_2$SO$_4$ and evaporated under reduced pressure. 1192 g (93%) of poly(ethylene glycol) (200) ditosylate was isolated as a clear oil.

Synthesis of INI-17

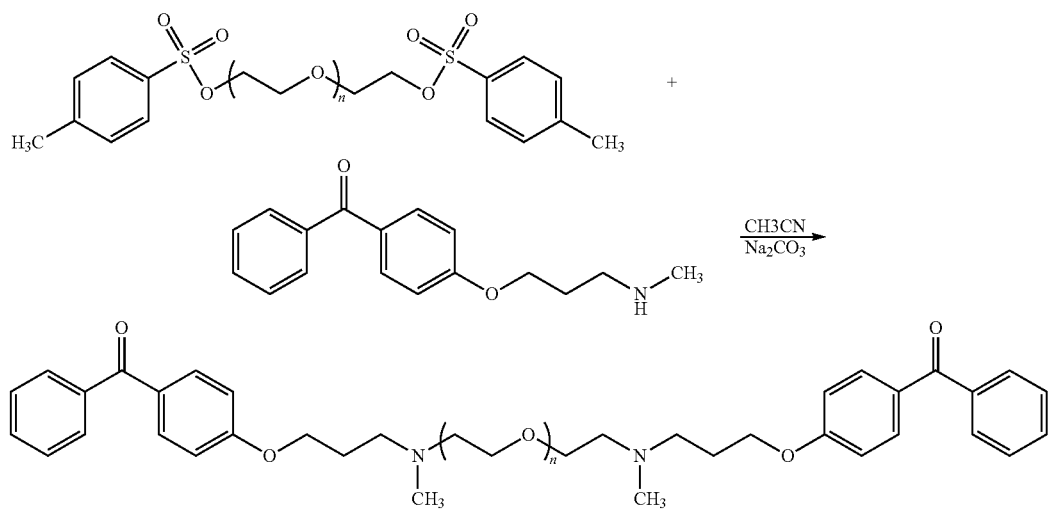

Poly(ethylene glycol) (200) ditosylate (7.7 g, 0.015 mol) was added dropwise to a mixture containing [4-(3-methylamino-propoxy)-phenyl-methanone] (8.1 g, 0.03 mol), sodium carbonate (3.2 g, 0.03 mol) and acetonitrile (60 mL). This mixture was heated at 55° C. and allowed to stir for 16 hours. The mixture was cooled to room temperature and filtered to remove the salts. The filtrate was evaporated under reduced pressure.

The oil was purified on Prochrom LC80 Column using methanol/distilled water/triethylamine/acetic acid (64/36/0.4%/0.8%) as eluent.

After evaporation of methanol, the pH of the aqueous layer was adjusted to 10 with sodium hydroxide, and extracted with dichloromethane. The organic layer was washed with a saturated solution of sodium chloride and dried over $MgSO_4$. Evaporation of the solvent provided 3.3 g of a yellow oil.

The Synthesis of INI-18

Synthesis of poly(ethylene glycol) (600) ditosylate

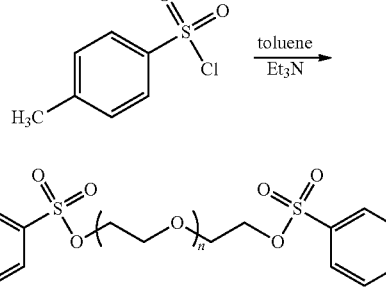

300 g of poly(ethylene glycol) (600) (0.5 mol) was dissolved in one liter toluene. 190 g (1 mol) tosyl chloride was added. A solution of 101 g (139 mL) triethyl amine in 200 mL toluene was added dropwise, while the temperature was kept below 25° C. The reaction was allowed to continue for 16 hours at room temperature. The precipitated salts were removed by filtration and the solvent was evaporated under reduced pressure. 453 g (~100%) of poly(ethylene glycol) (600) ditosylate was isolated.

Synthesis of INI-18

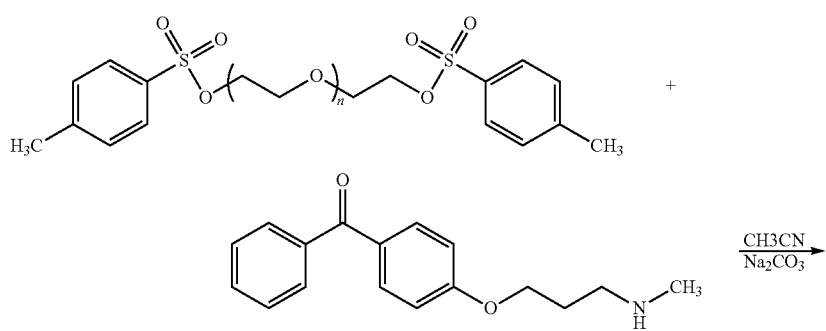

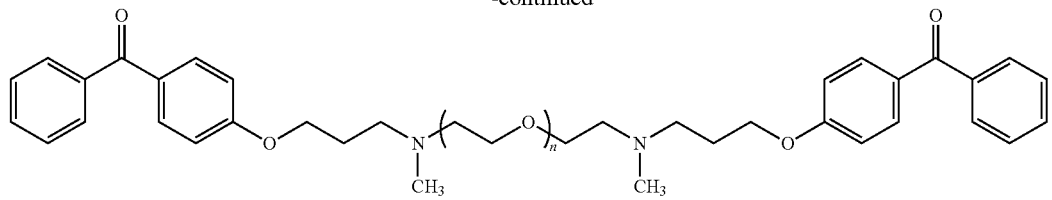

Poly(ethylene glycol) (600) ditosylate (13.7 g, 0.015 mol) was added dropwise to a mixture containing [4-(3-methylamino-propoxy)-phenyl-methanone] (8.1 g, 0.03 mol), sodium carbonate (3.2 g, 0.03 mol) and acetonitrile (60 mL). This mixture was heated at 55° C. and allowed to stir for 5 hours. The mixture was cooled to room temperature and filtered to remove the salts. The filtrate was evaporated under reduced pressure. The oil was purified on Prochrom LC80 Column using methanol/distilled water/triethylamine/acetic acid (64/36/0.4%/0.8%) as eluent. After evaporation of methanol, the pH of the aqueous layer was adjusted to 10 with sodium hydroxide, and extracted with dichloromethane. The organic layer was washed with a saturated solution of sodium chloride and dried over MgSO4. Evaporation of the solvent provided 2.88 g of a yellow oil.

The Synthesis of INI-19

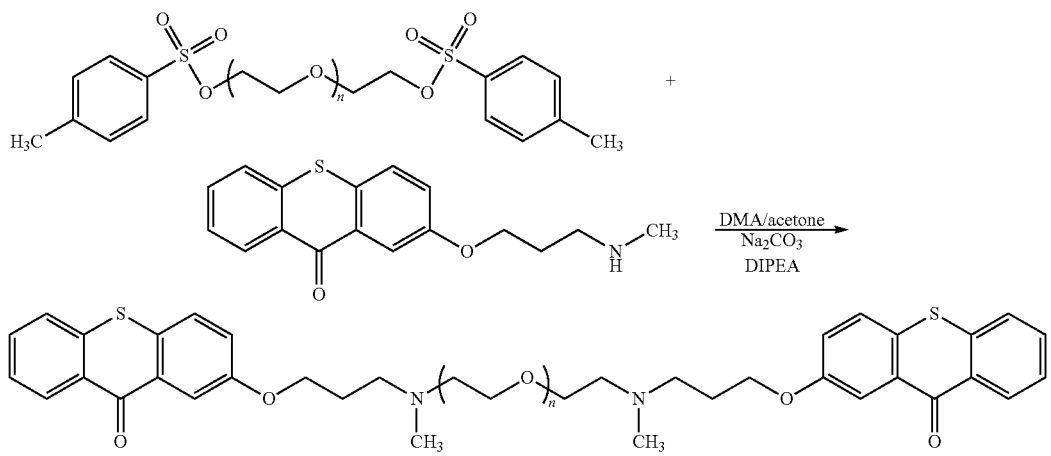

Poly(ethylene glycol) (600) ditosylate (3.2 g, 0.0035 mol) was added dropwise to a mixture containing 2-(3-methylamino-propoxy)-thioxanthen-9-one (2.1 g, 0.007 mol), sodium carbonate (0.7 g, 0.007 mol), N,N-diisopropylethylamine (0.9 g, 0.007 mol), acetone (150 mL) and dimethylacetamide (6 mL). This mixture was heated to reflux and allowed to stir for 16 hours. The mixture was cooled to room temperature and the solvent was evaporated under reduced pressure.

The product was purified on Prochrom LC80 Column using methanol/distilled water/triethylamine/acetic acid (67/33/0.29%/0.84%) as eluent.

After evaporation of methanol, the pH of the aqueous layer was adjusted to 10 with ammonia, and extracted with dichloromethane. The organic layer was separated and dried over MgSO4. Evaporation of the solvent provided 1.09 g of a yellow oil.

The Synthesis of INI-21

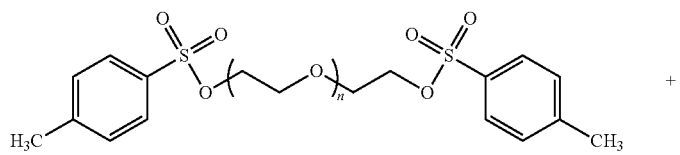

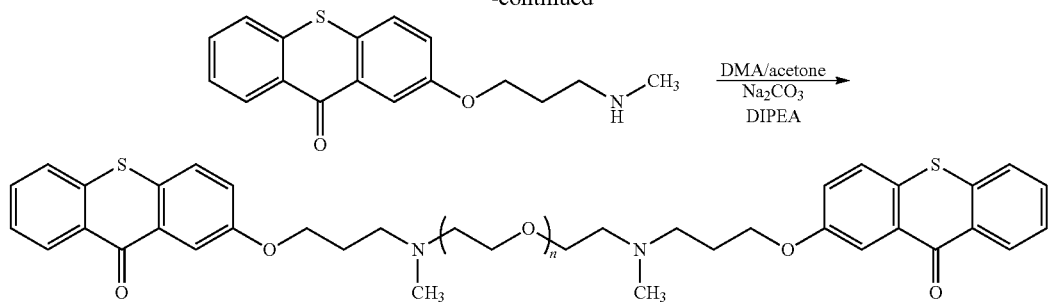

Poly(ethylene glycol) (200) ditosylate (1.8 g, 0.0035 mol) was added drop wise to a mixture containing 2-(3-methylamino-propoxy)-thioxanthen-9-one (2.1 g, 0.007 mol), sodium carbonate (0.7 g, 0.007 mol), N,N-diisopropylethylamine (0.9 g, 0.007 mol), acetone (150 mL) and dimethylacetamide (6 mL). This mixture was heated to reflux and allowed to stir for 16 hours. The mixture was cooled to room temperature and the solvent was evaporated under reduced pressure.

The product was purified on Prochrom LC80 Column using methanol/distilled water/triethylamine/acetic acid (70/30/0.29%/0.84%) as eluent.

After evaporation of methanol, the pH of the aqueous layer was adjusted to 10 with ammonia, and extracted with dichloromethane. The organic layer was separated and dried over MgSO4. Evaporation of the solvent provided 976 mg of a yellow oil.

Example 2

This example illustrates the reduction in extractable residues of the photoinitiator by using a multifunctional Type II photoinitiator according to a preferred embodiment of the present invention in the absence of a co-initiator.

Preparation of Radiation Curable Compositions

The inventive radiation curable compositions INV-1 to INV-3 and the comparative radiation curable compositions COMP-1 and COMP-2 were prepared according to Table 4. The weight % (wt %) of the different components was based on the total weight of the radiation curable composition.

TABLE 4

| wt % of: | INV-1 | INV-2 | INV-3 | COMP-1 | COMP-2 |
|---|---|---|---|---|---|
| INI-2 | 14.0 | — | — | — | — |
| INI-3 | — | 22.5 | — | — | — |
| INI-1 | — | — | 18.5 | — | — |
| COMPINI-1 | — | — | — | 10.0 | — |
| COMPCOINI-1 | — | — | — | — | 9.0 |
| COMPINI-2 | — | — | — | — | 11.0 |
| DPGDA | 44.0 | 35.5 | 39.5 | 48.0 | 38.0 |
| TMPTA | 40.0 | 40.0 | 40.0 | 40.0 | 40.0 |
| Dibutyl phthalate | 2.0 | 2.0 | 2.0 | 2.0 | 2.0 |

Dibutyl phthalate was added to the radiation curable compositions so that it could be used as an internal reference for the analysis of extractable residues.

Preparation of Coated Samples

The comparative radiation curable compositions COMP-1 and COMP-2 and the inventive radiation curable compositions INV-1 to INV-3 were coated on an unsubbed 100 mm PET substrate using a bar coater and a 10 mm wired bar. The coatings were cured using a Fusion DRSE-120 conveyer, equipped with a Fusion VPS/1600 lamp (D-bulb), which transported the samples under the UV-lamp on a conveyer belt at a speed of 20 m/min.

The curing speed was determined for the comparative radiation curable compositions COMP-1 and COMP-2 and the inventive radiation curable compositions INV-1 to INV-3. The results are summarized in Table 5.

TABLE 5

| Radiation curable composition | Curing speed (% of the maximum output) | Viscosity (mPa · s) |
|---|---|---|
| INV-1 | 130 | 43 |
| INV-2 | 50 | 76 |
| INV-3 | 55 | 62 |
| COMP-1 | 65 | 26 |
| COMP-2 | 45 | 31 |

From Table 5, it should be clear that all curable compositions, both comparative and inventive, cure well enough to determine extractable residues and have a viscosity within a jettable range.

The Extraction Procedure:

Two samples of 7.068 cm$^2$ of INV-1 to INV-3 and COMP-1 and COMP-2 were put into a 50 mL beaker and extracted with 4.5 mL acetonitrile, using ultrasound for 30 minutes. The extract was transferred into a 5 mL volumetric flask. The samples were rinsed twice with a small amount of acetonitrile and the rinsing solvent was transferred into the 5 mL volumetric flask until the volume was adjusted to 5 mL. The solution was thoroughly mixed and filtered over a 0.45 mm filter. 10 mL of each sample was injected on the HPLC.

The Chromatographic Method:

An Alltima C18 5 mm column (150×3.2 mm), supplied by Alltech, was used. A flow rate of 0.5 mL/min was used at a temperature of 40° C. A DAD detector at 291 nm was used to detect the extracted initiator and initiator fragments.

The following HPLC-method was used for all samples.

Eluent A: $H_2O+0.02M$ $KH_2PO_4$ pH=2.5 using $H_3PO_4$

Eluent B: $H_2O+0.02M$ $KH_2PO_4$ pH=2.5 using $H_3PO_4$/$CH_3CN$ [40/60] (v/v)

Eluent C: $H_2O$/$CH_3CN$ [40/60] (v/v)

Eluent D: $H_2O$/$CH_3CN$ [10/90] (v/v)

Gradient (end run=38 min)

TABLE 6

| Time (min) | % eluent A | % eluent B | % eluent C | % eluent D |
|---|---|---|---|---|
| 0 | 70 | 30 | 0 | 0 |
| 6 | 70 | 30 | 0 | 0 |
| 11 | 0 | 100 | 0 | 0 |
| 20 | 0 | 100 | 0 | 0 |
| 21 | 0 | 0 | 100 | 0 |
| 24 | 0 | 0 | 100 | 0 |
| 25 | 0 | 0 | 0 | 100 |
| 30 | 0 | 0 | 0 | 100 |
| 31 | 70 | 30 | 0 | 0 |
| 38 | 70 | 30 | 0 | 0 |

Assumptions made to calculate the amount of extractable residues:
- In each sample, all peaks, showing the same UV-VIS-spectrum as the reference benzophenone comparative initiator 2, were integrated to take potential degradation products from the different initiators, which become extractable, into account.
- To calculate the amount of extractable residues, expressed as mg/m$^2$, it was assumed that the average molecular weight of all compounds taken into account remained unchanged, compared to the original initiator, which for the polymeric initiators probably leads to an overestimation of the extractable residues.
- The concentration was determined in comparison with a reference sample of a known concentration of each comparative and inventive initiator, eluted under the same conditions as the extracted samples.
- A total coating weight of 10 g/m$^2$ was assumed for each sample.

The results are summarized in Table 7. The wt % of extracted initiator is based on the total wt % of the initiator of the original radiation curable composition. The comparative coinitiator COMPCOINI-1 in COMP-2 is not detectable under these chromatographic conditions.

TABLE 7

| Radiation curable composition | Extractable residues (mg/m$^2$) | wt % of extracted initiator |
|---|---|---|
| INV-1 | 160 | 11 |
| INV-2 | 308 | 13 |
| INV-3 | 214 | 11 |
| COMP-1 | 380 | 38 |
| COMP-2 | 730 | 66 |

From Table 7, one can see that the extraction of the multifunctional Type II photoinitiator is strongly reduced.

Example 3

This example illustrates the improved curing speed of the initiators according to a preferred embodiment of the present invention compared to the hyperbranched polymeric initiators, disclosed in EP 1674499 A (AGFA)).

Preparation of Radiation Curable Compositions

The inventive radiation curable compositions INV-4 to INV-6 and comparative radiation curable compositions COMP-3 to COMP-6 were prepared according to Table 8. The weight % (wt %) was based on the total weight of the radiation curable composition. The comparative initiators COMPINI-3 to COMPINI-6 correspond to the hyperbranched polymeric photoinitiators IS-1 to IS-4 from Example 1 in EP 1674499 A (AGFA).

TABLE 8

| wt % of: | INV-4 | INV-5 | INV-6 | COMP-3 | COMP-4 | COMP-5 | COMP-6 |
|---|---|---|---|---|---|---|---|
| INI-2 | 14.0 | — | — | — | — | — | — |
| INI-3 | — | 22.5 | — | — | — | — | — |
| INI-1 | — | — | 18.5 | — | — | — | — |
| COMPINI-3 | — | — | — | 18.0 | — | — | — |
| COMPINI-4 | — | — | — | — | 18.0 | — | — |
| COMPINI-5 | — | — | — | — | — | 18.0 | — |
| COMPINI-6 | — | — | — | — | — | — | 18.0 |
| DPGDA | 44.0 | 35.5 | 39.5 | 40.0 | 40.0 | 40.0 | 40.0 |
| TPGDA | 40.0 | 40.0 | 40.0 | 40.0 | 40.0 | 40.0 | 40.0 |
| Dibutyl phthalate | 2.0 | 2.0 | 2.0 | 2.0 | 2.0 | 2.0 | 2.0 |

Preparation of Coated Samples

The comparative radiation curable compositions COMP-3 to COMP-6 and the inventive radiation curable compositions INV-4 to INV-6 were coated on an unsubbed 100 mm PET substrate using a bar coater and a 10 mm wired bar. The coatings were cured using a Fusion DRSE-120 conveyer, equipped with a Fusion VPS/I600 lamp (D-bulb), which transported the samples under the UV-lamp on a conveyer belt at a speed of 20 m/min.

The curing speed was determined for the comparative radiation curable compositions COMP-3 to COMP-6 and the inventive radiation curable compositions INV-4 to INV-6. The results are summarized in Table 9. The comparative radiation curable compositions COMP-3 to COMP-6 were also cured under exclusion of oxygen.

TABLE 9

| Radiation curable composition | Curing speed (% of the maximum output) | | Viscosity (mPa · s) |
|---|---|---|---|
| | Under Air | Under N$_2$ | |
| INV-4 | 130 | Not tested | 43 |
| INV-5 | 50 | Not tested | 76 |
| INV-6 | 55 | Not tested | 62 |
| COMP-3 | >200 | 50 | 53 |
| COMP-4 | >200 | 50 | 74 |
| COMP-5 | >200 | 50 | 54 |
| COMP-6 | >200 | 50 | 49 |

From Table 9, it becomes apparent that the photoinitiators, according to preferred embodiments of the present invention are significantly more efficient, compared to the hyperbranched photoinitiators in EP 1674499 A (AGFA) allowing fast curing under ambient atmosphere.

Example 4

This example illustrates the importance of the design in the linking group L of the multifunctional Type II photoinitiators according to preferred embodiments of the present invention.

The Synthesis of Comparative Initiators 7 to 11

The synthesis of 4-(2-(N-carboxyethyl, N-ethylamino)ethoxy)benzophenone

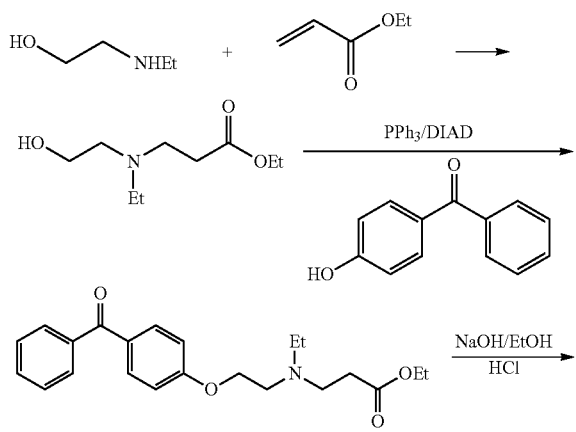

20 mL (0.204 mol) of 2-ethylaminoethanol and 44.2 mL (0.408) of ethyl acrylate was stirred at room temperature for 2 days. After removing most of the excess of ethyl acrylate under vacuum, toluene was added to help to get rid of the residual ethyl acrylate. Pure product could be obtained by distillation under reduced pressure (83.5° C./2 mbar). Mw=189.26, Yield: 31.4 g (81%).

21.3 g (0.136 mol) of ethyl 3-(N-(2-hydroxyethyl), N-ethylamino)propionate, 26.8 g (0.162 mol) of 4-hydroxybenzophenone and 53.3 g (0.203 mol) of triphenyl phosphine are dissolved in 500 mL of anhydrous THF. The solution was cooled to 0° C. and then 39.8 mL (0.203 mol) of diisopropyl azodicarboxylate (DIAD) was added slowly. After the addition of DIAD, the reaction was allowed to react at room temperature for 24 hours. Most of THF was removed under reduced pressure and the concentrated solution was dissolved in dichloromethane. The mixture was extracted with 0.5 N NaOH and water. The organic fraction is dried over MgSO₄ and the solvent is removed under reduced pressure. The crude mixture was dissolved in 200 mL of ethanol and 17 g (0.424 mol) of NaOH was added. The hydrolysis was allowed to continue for 24 hours at room temperature. After completion of the hydrolysis, dichloromethane was added and the mixture was extracted with water. The aqueous layer was extracted four times with dichloromethane and acidified to pH=2. The aqueous layer was extracted with butanol. The butanol extract was evaporated under reduced pressure. The obtained yellow oil was precipitated in diethyl ether twice, then hot acetone was used to dissolve the precipitate. After the solution was kept at room temperature for one or two days, a precipitate appeared. The white precipitate was washed with cold acetone, and then dried at 40° C. under vacuum. The pure product of HCl salt of 4-(2-(N-carboxyethyl, N-ethylamino) ethoxy)benzophenone was obtained as yellowish powder. Mw=378, yield: 26 g (51%).

Comparative Initiator 7

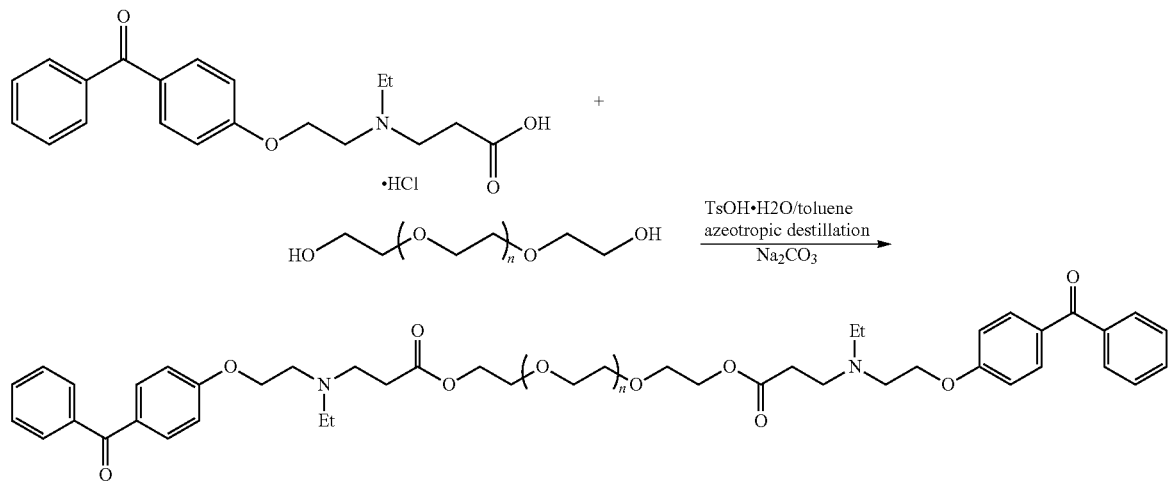

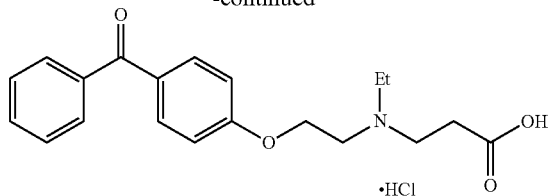

where n=3 on average.

0.26 g (1.3 mmol) of polyethylene glycol 200 1 g (2.8 mmol) of the HCl salt of 4-(2-(N-carboxyethyl, N-ethylamino)ethoxy)benzophenone and 1 g (5.1 mmol) of toluenesulfonic acid monohydrate were added into a one-neck flask equipped with Dean-Stark and condenser. Then 10 mL of toluene was added. The mixture was put into the oil-bath thermostated at 148° C. and stirred for 4 h. The reaction mixture was diluted with 50 mL EtOAc and extracted twice with 50 mL 1M Na₂CO₃. Finally the organic layer was dried over anhydrous magnesium sulphate. The solvent was evaporated to afford a brown oil. 1.03 g (93%) of comparative initiator 7 was isolated.

Comparative Initiator 8

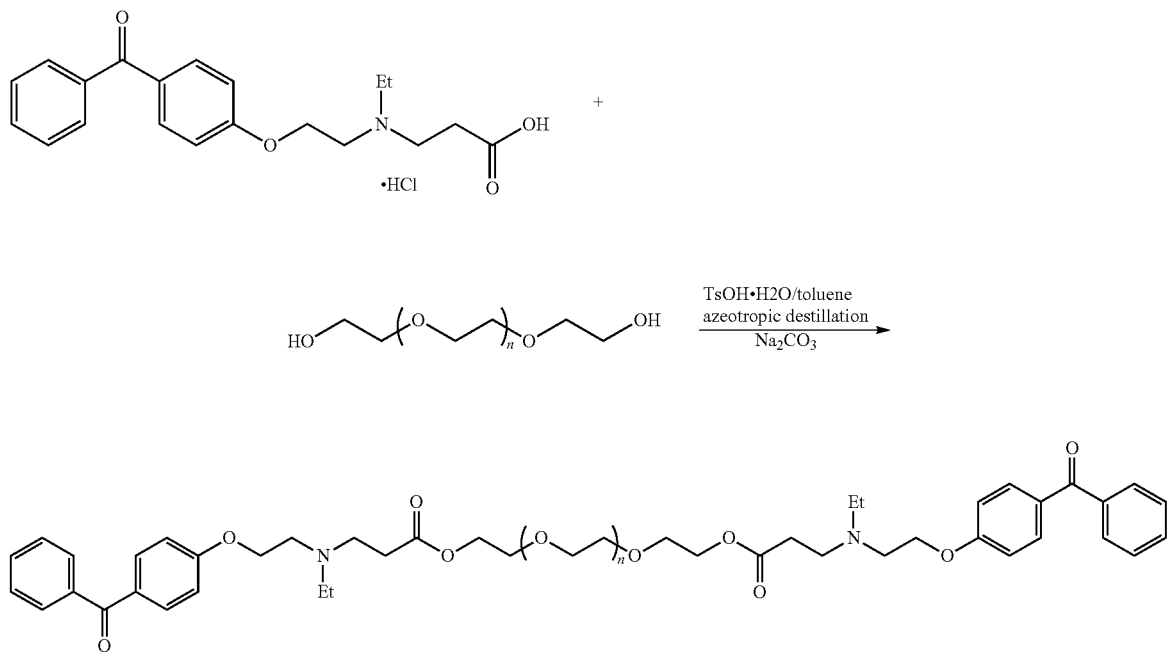

0.52 g (1.3 mmol) of polyethylene glycol 400 1 g (2.8 mmol) of the HCl salt of 4-(2-(N-carboxyethyl, N-ethylamino)ethoxy)benzophenone and 1 g (5.1 mmol) of toluenesulfonic acid monohydrate were added into a one-neck flask equipped with Dean-Stark and condenser. Then 10 mL of toluene was added. The mixture was put into the oil-bath thermostated at 148° C. and stirred for 4 h. The reaction mixture was diluted with 50 mL EtOAc and extracted twice with 50 mL 1M $Na_2CO_3$. Finally the organic layer was dried over anhydrous magnesium sulphate. The solvent was evaporated to afford a brown oil. 1.15 g (84%) of comparative initiator 8 was isolated.

Comparative Initiator 9

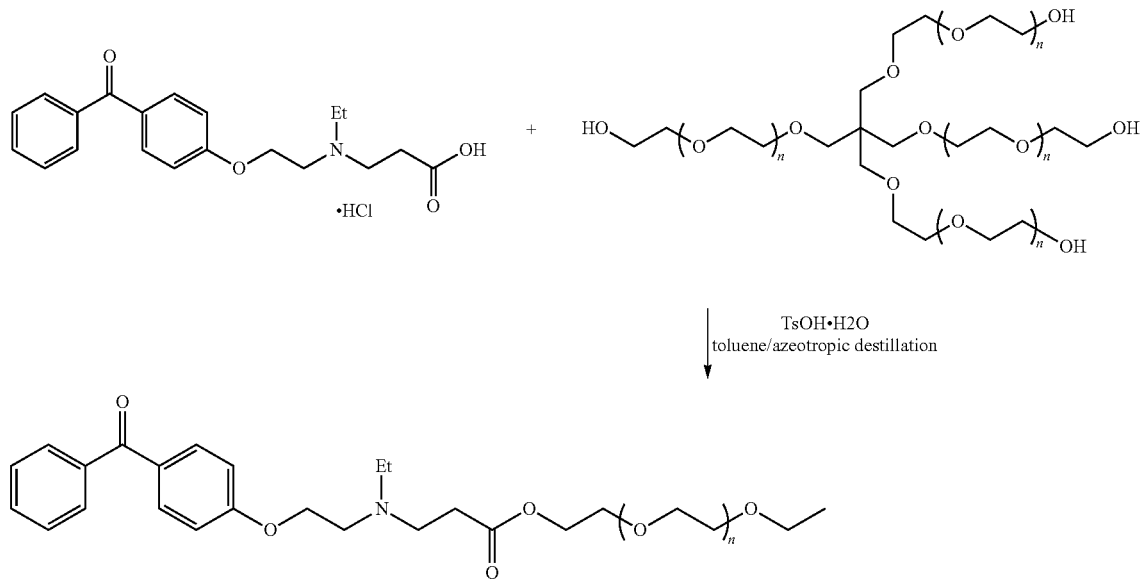

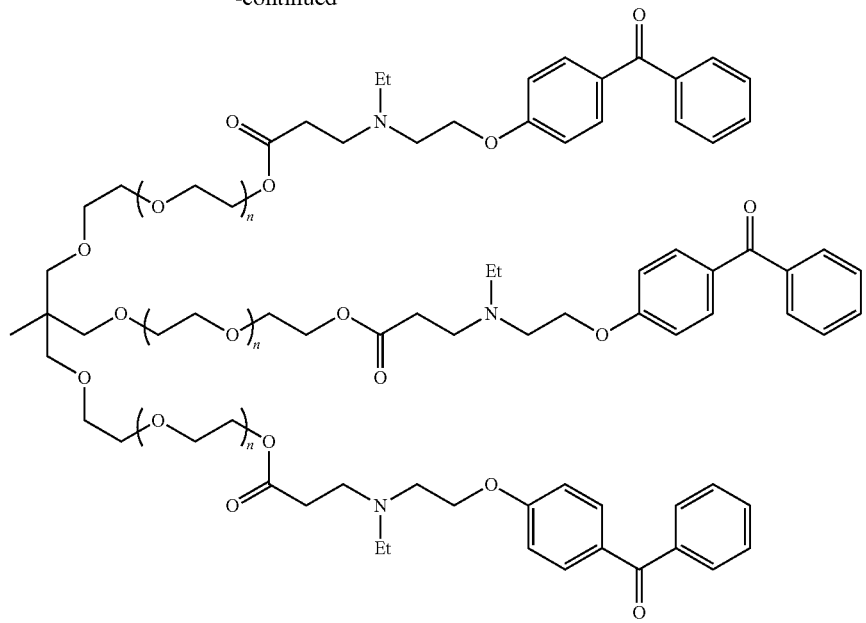

A mixture of 3-{[2-(4-benzoyl-phenoxy)-ethyl]-ethyl-amino}-propionic acid (1.2 g, 3.5 mmol), pentaerythritol ethoxylate (15/4 EO/OH), Mn~797 (0.7 g, 0.875 mmol) and p-toluenesulfonic acid monohydrate (0.9 g, 4.8125 mol) in toluene (40 mL) was heated at reflux for 6 hours while water was removed azeotropically. The reaction mixture was cooled to room temperature and the toluene phase was decanted off. The residual oil was brought in a mixture of ethyl acetate (25 mL), an aqueous solution of sodium hydroxide (1M) (5 mL) and distilled water (20 mL). The organic layer was separated, washed with water and dried on MgSO$_4$. Evaporation of the solvent provided 1.3 g of a brown oil.

Comparative Initiator 10

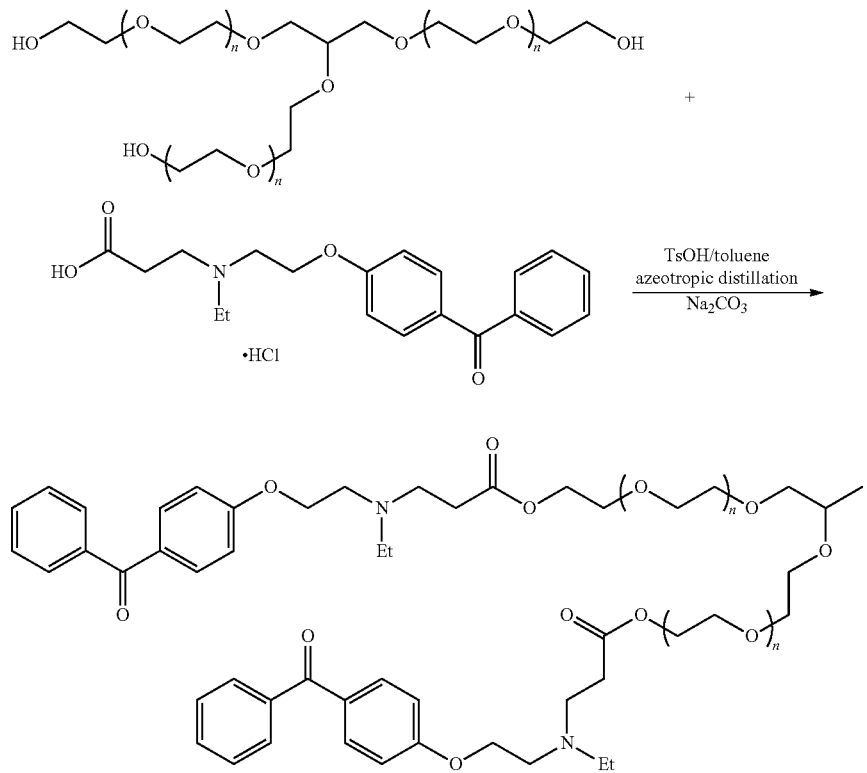

-continued

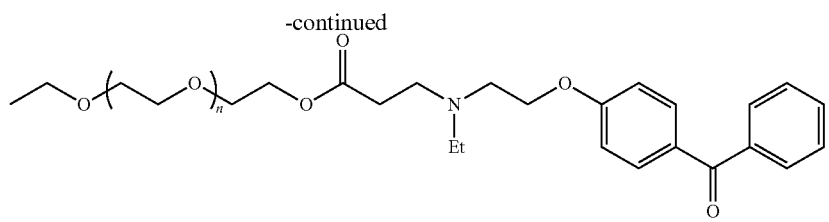

2.5 g (2.6 mmol) glycerol ethoxylate (average molecular weight 950), 3 g (8.6 mmol) 3-{[3-(4-benzoylphenoxy)-propyl]-methyl-amino}-propionic acid and 2.5 g (13 mmol) p.-toluene sulfonic acid monohydrate were dissolved in 30 mL toluene. The mixture was refluxed for 8 hours, while water was removed azeotropically. The mixture was diluted with 100 mL 1M $Na_2CO_3$ and 100 mL ethyl acetate. The organic fraction was isolated and dried over $MgSO_4$. The solvent was removed under reduced pressure and 4.5 g of comparative initiator 10 was isolated.

Preparation of Radiation Curable Compositions

The inventive radiation curable compositions INV-7 to INV-9 and comparative radiation curable compositions COMP-7 to COMP-10 were prepared according to Table 10. The weight % (wt %) was based on the total weight of the radiation curable composition.

TABLE 10

| wt % of | INV-7 | INV-8 | INV-9 | COMP-7 | COMP-8 | COMP-9 | COMP-10 |
|---|---|---|---|---|---|---|---|
| INI-2 | 14.0 | — | — | — | — | — | — |
| INI-3 | — | 22.5 | — | — | — | — | — |
| INI-1 | — | — | 18.5 | — | — | — | — |
| COMPINI-7 | — | — | — | 10.0 | — | — | — |
| COMPINI-8 | — | — | — | — | 12.5 | — | — |
| COMPINI-9 | — | — | — | — | — | 20.0 | — |
| COMPINI-10 | — | — | — | — | — | — | 16.0 |
| DPGDA | 44.0 | 35.5 | 39.5 | 48.0 | 45.5 | 38.0 | 42.0 |
| TMPTA | 40.0 | 40.0 | 40.0 | 40.0 | 40.0 | 40.0 | 40.0 |
| Dibutyl phthalate | 2.0 | 2.0 | 2.0 | 2.0 | 2.0 | 2.0 | 2.0 |

Preparation of Coated Samples

The comparative radiation curable compositions COMP-7 to COMP-10 and the inventive radiation curable compositions INV-7 to INV-9 were coated on an unsubbed 100 mm PET substrate using a bar coater and a 10 mm wired bar. The coatings were cured using a Fusion DRSE-120 conveyer, equipped with a Fusion VPS/1600 lamp (D-bulb), which transported the samples under the UV-lamp on a conveyer belt at a speed of 20 m/min.

The curing speed was determined for comparative radiation curable compositions COMP-7 to COMP-10 and the inventive radiation curable compositions INV-7 to INV-9. The results are summarized in Table 11.

TABLE 11

| Radiation curable composition | Curing speed (% of the maximum output) |
|---|---|
| INV-7 | 130 |
| INV-8 | 50 |
| INV-9 | 55 |
| COMP-7 | >200 |
| COMP-8 | >200 |
| COMP-9 | 160 |

TABLE 11-continued

| Radiation curable composition | Curing speed (% of the maximum output) |
|---|---|
| COMP-10 | 170 |

From Table 11, it becomes apparent that the linking group has a significant impact on the curing speed of the radiation curable formulation. A linking group according to a preferred embodiment of the present invention results in a reasonable to high curing speed, while a linking group, not according to the present invention results in a rather poor to very poor curing speed.

Example 5

This example illustrates the influence of the multifunctional Norrish type-II initiators according to preferred embodiments of the present invention on the amount of volatile components desorbed from the layer, expressed as the TDE-level.

Preparation of Radiation Curable Compositions

The inventive radiation curable compositions INV-10 to INV-13 and comparative curable composition COMP-12 were prepared according to Table 12. The weight % (wt %) was based on the total weight of the radiation curable composition.

TABLE 12

| wt % of | INV-10 | INV-11 | INV-12 | INV-13 | COMP-12 |
|---|---|---|---|---|---|
| VEEA | 67.0 | 62.0 | 67.0 | 62.0 | 74.5 |
| M600 | 20.0 | 20.0 | 20.0 | 20.0 | 20.0 |
| INI-3 | 10.0 | 15.0 | — | — | — |
| INI-4 | — | — | 10.0 | 15.0 | — |
| Irgacure 127 | — | — | — | — | 2.5 |
| Surfactant A | 3.0 | 3.0 | 3.0 | 3.0 | 3.0 |

Preparation of Coated Samples

The free radical curable liquids COMP-12 and INV-10 to INV-13 were coated on a PET100 substrate using a bar coater and a 10 mm wired bar. Each coated sample was cured using a Fusion DRSE-120 conveyer, equipped with a Fusion VPS/ 1600 lamp (D-bulb), which transported the samples twice under the UV-lamp on a conveyer belt at a speed of 10 m/min.

To cure under nitrogen inerting conditions, the coated sample was mounted on a metal plate and on top of the plate a metal frame of 1 cm height with a non UV-absorbing quartz glass window was placed, so that a sealed chamber was formed with the coated sample inside. Then, the trapped air in the chamber was replaced by nitrogen gas by introducing pure nitrogen gas into the chamber for 30 seconds and the coated sample was placed on the conveyer belt.

The curing degree was determined for the free radical curable liquids COMP-11 and INV-10 to INV-13. The results are summarized in Table 13.

TABLE 13

| Radiation curable composition | Curing under air | Curing under $N_2$ |
| --- | --- | --- |
| INV-10 | Fully cured | Fully cured |
| INV-11 | Fully cured | Fully cured |
| INV-12 | Fully cured | Fully cured |
| INV-13 | Fully cured | Fully cured |
| COMP-11 | Not cured | Fully cured |

The samples cured under nitrogen inerting conditions were used to determine the TDE-level. The results for the free radical curable liquids COMP-11 and INV-10 to INV-13 are summarized in Table 14. Coupling of the GC with mass spectroscopy revealed that none of the volatile residues were related to the initiators according to preferred embodiments of the present invention.

TABLE 14

| Radiation curable composition | TDE-level (ppm) |
| --- | --- |
| INV-10 | 1060 |
| INV-11 | 880 |
| INV-12 | 946 |
| INV-13 | 784 |
| COMP-11 | 510 |

From the results in Table 13 and Table 14, it can be concluded that the multifunctional Norrish type-II initiators according to preferred embodiments of the present invention, result in a high curing speed over a broad range of curing circumstances, while still maintaining a low level of volatile residues.

Example 6

This example illustrates that multifunctional Norrish type-II initiators according to preferred embodiments of the present invention are suitable to formulate pigmented radiation curable inkjet inks in a CMYK ink set which are curable both under air and under nitrogen.

Preparation of Radiation Curable Compositions

The inventive radiation curable inks INV-14 to INV-21 were prepared according to Table 15. The weight % (wt %) was based on the total weight of the radiation curable ink.

TABLE 15

| wt % of | INV-14 | INV-15 | INV-16 | INV-17 | INV-18 | INV-19 | INV-20 | INV-21 |
| --- | --- | --- | --- | --- | --- | --- | --- | --- |
| VEEA | 49.8 | 47.0 | 52.0 | 52.0 | 49.8 | 47.0 | 52.0 | 52.0 |
| M600 | 20.0 | 20.0 | 20.0 | 20.0 | 20.0 | 20.0 | 20.0 | 20.0 |
| Surfactant A | 3.0 | 3.0 | 3.0 | 3.0 | 3.0 | 3.0 | 3.0 | 3.0 |
| Disp K | 17.2 | — | — | — | 17.2 | — | — | — |
| Disp M | — | 20.0 | — | — | — | 20.0 | — | — |
| Disp Y | — | — | 15.0 | — | — | — | 15.0 | — |
| Disp C | — | — | — | 15.0 | — | — | — | 15.0 |
| INI-3 | 10.0 | 10.0 | 10.0 | 10.0 | — | — | — | — |
| INI-4 | — | — | — | — | 10.0 | 10.0 | 10.0 | 10.0 |

The pigment dispersions Disp K, Disp M, Disp Y and Disp C were prepared in the following manner.

Disp K

A concentrated pigment dispersion Disp K was made by mixing 466.7 g of a 30 wt % solution of the polymeric dispersant in S35000 in DPGDA, 86.3 g of DPGDA, 7.0 g of the stabilizer GENORAD™ 16, 102.9 g of Special Black 550 and 37.1 g of HOSTAPERM™ Blue P-BFS for 30 minutes using a DISPERLUX™ YELLOW075 (from DISPERLUX S.A.R.L., Luxembourg) and subsequently milling this mixture in a Eiger Lab Bead mill (from EIGER TORRANCE Ltd.) using yttrium-stabilized zirconium oxide-beads of 0.4 mm diameter ("high wear resistant zirconia grinding media" from TOSOH Co.). The bead mill is filled for 52% with the grinding beads and water-cooled during milling at 4250 rpm for 90 minutes. After milling the dispersion was separated from the beads using a filter cloth. The concentrated pigment dispersion Disp K had an average particles size of 111 nm measured with a MALVERN™ nano-S particle size analyzer and a viscosity of 81 mPa·s at 10 s$^{-1}$ at 25° C.

Disp M

A concentrated pigment dispersion Disp M was made by mixing 466.7 g of a 30 wt % solution of the polymeric dispersant in S35000 in VEEA, 86.3 g of VEEA, 7.0 g of the stabilizer GENORAD™ 16 and 140.0 g of CINQUASIA™ Magenta RT-355-D for 30 minutes using a DISPERLUX™ YELLOW075 (from DISPERLUX S.A.R.L., Luxembourg) and subsequently milling this mixture in a Eiger Lab Bead mill (from EIGER TORRANCE Ltd.) using yttrium-stabilized zirconium oxide-beads of 0.4 mm diameter ("high wear resistant zirconia grinding media" from TOSOH Co.). The bead mill is filled for 52% with the grinding beads and water-cooled during milling at 4250 rpm for 220 minutes. After milling the dispersion was separated from the beads using a filter cloth. The concentrated pigment dispersion Disp M had an average particles size of 96 nm measured with a MALVERN™ nano-S particle size analyzer and a viscosity of 306 mPa·s at 10 s$^{-1}$ at 25° C.

Disp Y

A concentrated pigment dispersion Disp Y was made by mixing 466.7 g of a 30 wt % solution of the polymeric dispersant in S35000 in VEEA, 86.3 g of VEEA, 7.0 g of the stabilizer GENORAD™ 16 and 140.0 g of PY150 for 30 minutes using a DISPERLUX™ YELLOW075 (from DISPERLUX S.A.R.L., Luxembourg) and subsequently milling this mixture in a Eiger Lab Bead mill (from EIGER TORRANCE Ltd.) using yttrium-stabilized zirconium oxide-beads of 0.4 mm diameter ("high wear resistant zirconia grinding media" from TOSOH Co.). The bead mill is filled for 52% with the grinding beads and water-cooled during milling at 4250 rpm for 220 minutes. After milling the dispersion was separated from the beads using a filter cloth. The concentrated pigment dispersion Disp Y had an average particles size of 136 nm measured with a MALVERN™ nano-S particle size analyzer and a viscosity of 275 mPa·s at 10 s$^{-1}$ at 25° C.

Disp C

A concentrated pigment dispersion Disp C was made by mixing 466.7 g of a 30 wt % solution of the polymeric dispersant in S35000 in VEEA, 86.3 g of VEEA, 7.0 g of the stabilizer GENORAD™ 16 and 140.0 g of HOSTAPERM™ Blue P-BFS for 30 minutes using a DISPERLUX™ YELLOW075 (from DISPERLUX S.A.R.L., Luxembourg) and subsequently milling this mixture in a Eiger Lab Bead mill (from EIGER TORRANCE Ltd.) using yttrium-stabilized zirconium oxide-beads of 0.4 mm diameter ("high wear resistant zirconia grinding media" from TOSOH Co.). The bead mill is filled for 52% with the grinding beads and water-cooled during milling at 4250 rpm for 220 minutes. After milling the dispersion was separated from the beads using a filter cloth. The concentrated pigment dispersion Disp Y had an average particles size of 113 nm measured with a MALVERN™ nano-S particle size analyzer and a viscosity of 129 mPa·s at 10 s$^{-1}$ at 25° C.

Preparation of Coated Samples

The free radical curable liquids INV-14 to INV-21 were coated on a PET100 substrate using a bar coater and a 10 mm wired bar. Each coated sample was cured using a Fusion DRSE-120 conveyer, equipped with a Fusion VPS/1600 lamp (D-bulb), which transported the samples twice under the UV-lamp on a conveyer belt at a speed of 10 m/min.

To cure under nitrogen inerting conditions, the coated sample was mounted on a metal plate and on top of the plate a metal frame of 1 cm height with a non UV-absorbing quartz glass window was placed, so that a sealed chamber was formed with the coated sample inside. Then, the trapped air in the chamber was replaced by nitrogen gas by introducing pure nitrogen gas into the chamber for 30 seconds and the coated sample was placed on the conveyer belt.

The curing degree and the viscosity were determined for the free radical curable inks INV-14 to INV-21.

The curing degree results and the viscosity of the free radical curable inks INV-14 to INV-21 are summarized in Table 16.

TABLE 16

| Radiation curable ink | Viscosity (mPa · s) | Curing under air | Curing under N$_2$ |
|---|---|---|---|
| INV-14 | 15.09 | Fully cured | Fully cured |
| INV-15 | 17.47 | Fully cured | Fully cured |
| INV-16 | 16.78 | Fully cured | Fully cured |

TABLE 16-continued

| Radiation curable ink | Viscosity (mPa · s) | Curing under air | Curing under N$_2$ |
|---|---|---|---|
| INV-17 | 11.03 | Fully cured | Fully cured |
| INV-18 | 15.86 | Fully cured | Fully cured |
| INV-19 | 22.6 | Fully cured | Fully cured |
| INV-20 | 18.39 | Fully cured | Fully cured |
| INV-21 | 12.18 | Fully cured | Fully cured |

From Table 16, it becomes clear that all the radiation curable inks cure well both under air and under nitrogen and are well within the viscosity range to be jettable.

Example 7

This example illustrates that radiation curable compositions including Norrish type-II initiators according to preferred embodiments of the present invention exhibit high curing speed in the absence of an amine synergist.

Preparation of Radiation Curable Compositions

The inventive radiation curable compositions INV-22 to INV-25 and comparative radiation curable composition COMP-12 were prepared according to Table 17. The weight % (wt %) was based on the total weight of the radiation curable compositions.

TABLE 17

| wt % of | INV-22 | INV-23 | INV-24 | INV-25 | COMP-12 |
|---|---|---|---|---|---|
| DPGDA | 44.5 | 37.5 | 43.5 | 36.0 | 37.0 |
| TMPTA | 40.0 | 40.0 | 40.0 | 40.0 | 40.0 |
| INI-17 | 13.5 | — | — | — | — |
| INI-18 | — | 20.5 | — | — | — |
| INI-21 | — | — | 14.5 | — | — |
| INI-19 | — | — | — | 22.0 | — |
| COMPINI-2 | — | — | — | — | 11.5 |
| COMPCOINI-1 | — | — | — | — | 9.5 |
| dibutyl phtalate | 2.0 | 2.0 | 2.0 | 2.0 | 2.0 |

Preparation of Coated Samples

The comparative radiation curable composition COMP-12 and the inventive radiation curable compositions INV-22 to INV-25 were coated on an unsubbed 100 μm PET, using a bar coated and a 10 μm wired bar. The coatings were cured using a Fusion DRSE-120 conveyer, equipped with a Fusion VPS/1600 lamp (D-bulb), which transported the samples under the UV-lamp on a conveyer belt at a speed of 20 m/min.

The curing speed was determined for inventive radiation curable compositions INV-22 to INV-25 and for comparative radiation curable composition COMP-12. The results are summarized in Table 18.

TABLE 18

| Radiation curable composition | Curing speed (% of the maximum output) |
|---|---|
| INV-22 | 45 |
| INV-23 | 35 |
| INV-24 | 65 |
| INV-25 | 95 |
| COMP-12 | 45 |

From Table 18, it can be concluded that the initiators according to preferred embodiments of the present invention show a good to excellent curing sensitivity.

While preferred embodiments of the present invention have been described above, it is to be understood that variations and modifications will be apparent to those skilled in the art without departing the scope and spirit of the present invention. The scope of the present invention, therefore, is to be determined solely by the following claims.

The invention claimed is:

1. A multifunctional Type II photoinitiator according to Formula (I):

Formula (I)

wherein X represents a structural moiety according to Formula (II):

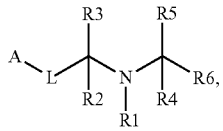

Formula (II)

wherein:

A represents a Norrish Type II initiating group;

L represents a divalent linking group positioning the Norrish Type II initiating group A and the CR2R3-group in a 1-5 to a 1-9 position wherein position 1 is defined as the first atom in the aromatic or alicyclic ring of A to which L is covalently bonded and the position 5 to 9 is defined as the carbon atom of the CR2R3-group to which L is covalently bonded, with the proviso that L does not contain an amine;

R1 represents an optionally substituted group selected from the group consisting of an alkyl group, an alkynyl group, an aralkyl group, an alkaryl group, an aryl group, and a heteroaryl group;

R2 to R6 each independently represent a hydrogen or an optionally substituted group selected from the group consisting of an alkyl group, an alkenyl group, an alkynyl group, an aralkyl group, an alkaryl group, an aryl group, and a heteroaryl group, with the proviso that at least one of R2 to R6 represents a hydrogen;

any two or three groups of the group selected from R1 to R6 and L may represent the necessary atoms to form a five to eight membered ring, and with the proviso that L is not substituted with a (meth)acrylate group and that none of R1 to R6 is substituted with an ethylenically unsaturated polymerizable group;

Q represents an n-valent linking group having a number average molecular weight of at most 5,000;

Q is bonded to each of the moieties X via a single bond to a group selected from R1 to R6, L, and A; and n represents an integer from 2 to 8.

2. The multifunctional Type II photoinitiator according to claim 1, wherein the Norrish Type II initiating group A is selected from the group consisting of an optionally substituted benzophenone and an optionally substituted thioxanthone.

3. The multifunctional Type II photoinitiator according to claim 2, including an optionally substituted benzophenone and an optionally substituted thioxanthone.

4. The multifunctional Type II photoinitiator according to claim 1, wherein the n-valent linking group Q includes at least one ethylene oxide and/or propylene oxide moiety.

5. The multifunctional Type II photoinitiator according to claim 1, wherein R1 is selected from the group consisting of a substituted or unsubstituted alkyl group and a substituted or unsubstituted aryl group.

6. The multifunctional Type II photoinitiator according to claim 5, wherein R1 represents an aryl group according to Formula (III):

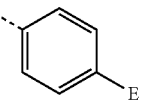

Formula (III)

wherein the dotted line represents a chemical bond to the nitrogen atom in Formula (II), and E represents a group selected from the group consisting of an ester, an aldehyde, a ketone, and an amide.

7. The multifunctional Type II photoinitiator according to claim 6, wherein the group E represents an ester group.

8. The multifunctional Type II photoinitiator according to claim 1, wherein the divalent linking group L is represented by the group —O—(CH$_2$)$_n$— with n representing an integer selected from 3 to 7.

9. A radiation curable composition comprising:
the multifunctional Type II photoinitiator according to claim 1.

10. The radiation curable composition according to claim 9, wherein the radiation curable composition is a radiation curable inkjet ink including a colorant.

11. A radiation curable ink set comprising:
the radiation curable composition according to claim 9.

12. An inkjet printing method comprising the steps of:
a) providing the radiation curable composition according to claim 9; and
b) at least partially curing the radiation curable composition.

13. The inkjet printing method according to claim 12, further comprising the step of:
applying the radiation curable composition to a substrate by flexographic printing; and
printing an inkjet ink upon the at least partially cured radiation curable composition.

14. The inkjet printing method according to claim 12, further comprising the step of:
jetting the radiation curable composition upon a substrate.

* * * * *